(12) United States Patent
Thomas et al.

(10) Patent No.: US 6,444,474 B1
(45) Date of Patent: Sep. 3, 2002

(54) MICROFLUIDIC SYSTEM FOR MEASUREMENT OF TOTAL ORGANIC CARBON

(75) Inventors: Ross C. Thomas, Superior; Eric D. Cravens, Broomfield; Michael T. Carter, Denver, all of CO (US)

(73) Assignee: Eltron Research, Inc., Boulder, CO (US)

(*) Notice: Subject to any disclaimer, the term of this patent is extended or adjusted under 35 U.S.C. 154(b) by 0 days.

(21) Appl. No.: 09/294,697

(22) Filed: Apr. 19, 1999

Related U.S. Application Data
(60) Provisional application No. 60/082,705, filed on Apr. 22, 1998.

(51) Int. Cl.[7] .............................................. G01N 33/00
(52) U.S. Cl. ...................... 436/146; 422/58; 422/68.1; 422/78; 422/80
(58) Field of Search ............... 422/50, 58, 68.1, 422/78, 80; 436/146

(56) References Cited

U.S. PATENT DOCUMENTS

| | | | |
|---|---|---|---|
| 3,224,837 A | 12/1965 | Moyat | |
| 3,607,071 A | * 9/1971 | Staffin et al. | 436/146 |
| 3,958,941 A | 5/1976 | Regan | 23/253 |
| 4,277,438 A | 7/1981 | Ejzak | 422/80 |
| 4,293,522 A | 10/1981 | Winkler | 422/80 |
| 4,619,902 A | 10/1986 | Bernard | 436/145 |
| 4,626,413 A | 12/1986 | Blades | 422/78 |
| 4,666,860 A | 5/1987 | Blades | 436/146 |
| 4,868,127 A | 9/1989 | Blades | 436/146 |
| 5,376,252 A | * 12/1994 | Ekström et al. | 204/299 R |
| 5,498,392 A | * 3/1996 | Wilding et al. | 422/68.1 |
| 5,500,071 A | * 3/1996 | Kaltenbach et al. | 156/272.8 |
| 5,514,253 A | * 5/1996 | Davis et al. | 205/782.5 |
| 5,637,469 A | 6/1997 | Wilding et al. | 435/7.21 |

(List continued on next page.)

FOREIGN PATENT DOCUMENTS

| | | |
|---|---|---|
| JP | 10288580 A  * | 10/1998 |
| WO | WO-91/16966 * | 10/1991 |
| WO | 94/35498 | 12/1995 |
| WO | 96/01999 | 1/1996 |

OTHER PUBLICATIONS

Al–Ekabi, H. and Serpone, N. (1988), "Kinetic Studies in Heterogeneous Photocatalysis. 1. Photocatalytic Degradation of Chlorinated Phenols in Aerated Aqueous Solutions over $TiO_2$ Supported on a Glass Matrix," J. Phys. Chem. 92:5726–5731.

Hitchman, M.L. et al. (1996), "Photoelectrochemical study of titanium dioxide films prepared by anodisation of titanium metal in sulfuric acid," J. Chem. Soc. Faraday Trans. 92:4049–4052.

Izumi, I. et al. (1980), "Heterogeneous Photocatalytic Oxidation of Hydrocarbons on Platinized $TiO_2$ Powders," J. Phys. Chem. 80:3207–3210.

(List continued on next page.)

*Primary Examiner*—Jill Warden
*Assistant Examiner*—Yelena Gakh
(74) *Attorney, Agent, or Firm*—Greenlee, Winner and Sullivan, P.C.

(57) ABSTRACT

This invention provides devices for the measurement of total organic carbon content in water samples. The device has a microfluidic sample cell with a sample channel for receiving a water sample wherein the water sample can be irradiated with UV radiation to oxidize organics to $CO_2$. The sample channel is sufficiently thin in the region irradiated to allow very rapid substantial mineralization of the organics in the sample. A photocatalyst, such as $TiO_2$ or platinized $TiO_2$ can be employed to speed sample oxidation. Substantial mineralization of a sample can be achieved in less than about 30 seconds, significantly decreasing the time required for making a TOC measurement. $CO_2$ generated by sample oxidation can be detected and/or quantitated by various methods, particularly by conductivity measurements or by infrared methods.

32 Claims, 14 Drawing Sheets

U.S. PATENT DOCUMENTS

| | | | | | |
|---|---|---|---|---|---|
| 5,855,850 | A | * | 1/1999 | Sittler | 422/98 |
| 5,858,195 | A | * | 1/1999 | Ramsey | 204/601 |
| 5,882,465 | A | * | 3/1999 | McReynolds | 156/285 |
| 5,885,470 | A | * | 3/1999 | Parce et al. | 216/33 |
| 5,904,824 | A | * | 5/1999 | Oh | 204/601 |
| 5,955,028 | A | * | 9/1999 | Chow et al. | 422/63 |
| 5,965,237 | A | * | 10/1999 | Bruin et al. | 428/156 |
| 6,057,149 | A | * | 5/2000 | Burns et al. | 435/287.2 |

OTHER PUBLICATIONS

Kim, D.H. and Anderson, M.A. (1994), "Photoelectrocatalytic Degradation of Formic Acid Using a Porous $TiO_2$ Thin–Film Electrode," Environ. Sci. Technol. 28:479–483.

Kim, D.H. et al. (1995), "Effects of Firing Temperature on Photocatalytic and Photoelectrocatalytic Properties of $TiO_2$," J. Env. Eng. 121:590–594.

Leitner, K. et al. (1986), "Photoelectrochemical Investigations of Passive Films on Titanium Electrodes," J. Electrochem. Soc. 133:1561–1568.

Loveland, J.W. (1963), "Conductometry and Oscillometry" in *Treatise on Analytical Chemistry, Part I. Theory and Practice,* Chapter 51, John Wiley & Sons, New York.

Manginell, R.P. et al. (Jun. 1996), "Selective, Pulsed CVD of Platinum on Microfilament Gas Sensors," IEEE Solid––State Sensor and Actuator Workshop, Hilton Head Island, South Carolina, pp. 23–27.

Mathews, R.W. (1987), "Photooxidation of Organic Impurities in Water Using Thin Films of Titanium Dioxide," J. Phys. Chem. 91:3328–3333.

Mathews, R.W. (1988), "Kinetics of Photocatalytic Oxidation of Organic Solutes over Titanium Dioxide," J. Catal. 111:264–272.

Matthews, R.W. et al. (1990), "Photocatalytic oxidation for total organic carbon analysis," Anal. Chim. Acta 233:171–179.

Mikula, M. et al. (1992), "Photoelectrochemical Properties of Anodic $TiO_2$ Layers Prepared by Various Current Densities," J. Electrochem. Soc. 139:3470–3474.

Morrison, S.R. (1980) *Electrochemistry at Semiconductor and Oxidized Metal Electrodes,* Plenum Press, New York, NY.

Poirier, S.J. and Wood, J.H. (1978) "A New Approach to the Measurement of Organic Carbon," American Laboratory, Dec., pp. 79–89.

Serpone, N. et al. (1986), "Photocatalysis over $TiO_2$ supported on a glass substrate," Solar Energy Materials 14:121–127.

Turchi, C.S. and Ollis, D.F. (1988), "Photocatalytic Reactor Design: An Example of Mass–Transfer Limitations with an Immobilized Catalyst," J. Phys. Chem. 92:6852–6853.

Turchi, C.S. and Ollis, D.F. (1990), "Photocatalytic Degradation of Organic Water Contaminants: Mechanisms Involving Hydroxyl Radical Attack," J. Catal. 122:178–192.

Wahl, A. et al. (1995), "Photoelectrochemical studies pertaining to the activitiy of $TiO_2$ towards photodegradation of organic compounds," J. Electroanal. Chem. 396:41–51.

* cited by examiner

MICROFLUIDIC SYSTEM FOR MEASUREMENT OF TOTAL ORGANIC CARBON

CROSS-REFERENCE TO RELATED APPLICATIONS

This application takes priority under U.S.C. 119(e) from U.S. provisional application serial No. 60/082,705, filed Apr. 22, 1998, which is incorporated in its entirety by reference herein to the extent not inconsistent herewith.

This invention was made at least in part with United States government funding through National Science Foundation Grant No. DMI-9660634. The United States government has certain rights in this invention.

FIELD OF THE INVENTION

This invention relates to microfluidic instruments for the measurement of total organic carbon (TOC) in water. More specifically the invention relates to rapid, real-time measurement of TOC.

BACKGROUND OF THE INVENTION

Highly purified water, often in large quantities, is a requirement for a variety of industries. The semiconductor industry, for example, has a particular need for highly purified water for cleaning or as a solvent in the production of integrated circuits. Pharmaceutical and chemical manufacture has a similar requirement for highly purified water. The presence of organic carbon compounds, even in trace amounts, in water used for manufacturing can be deleterious to the quality or purity of products made and the efficiency of manufacturing processes.

Coupled to the requirement for highly purified water is a requirement for accurate, reproducible assessment of water purity. Detection and quantitation of trace contaminants in water can be used to test process water quality, to validate water purification systems and to avoid introduction of contaminated water into process streams or reactions.

The measurement of total organic carbon (TOC) concentration is also used to assess contamination of potable water, municipal water supplies and in industrial and municipal effluents and waste waters.

The organic carbon content of water can be determined by methods which initially oxidize the organic carbon in a sample to $CO_2$ and then determine the amount of $CO_2$ generated in the sample. Organics in water samples can be oxidized in a number of ways by combustion, by use of chemical oxidation agents and/or by UV radiation. In total organic carbon (TOC) analysis, $CO_2$ can be quantitated using infrared (IR) absorption techniques, conversion to methane followed by flame ionization or by measurement of sample conductivity. See, e.g., S. J. Poirier and J. H. Wood (1978) "A New Approach to the Measurement of Organic Carbon," American Laboratory, December:79–89, for an overview of such techniques.

Conventional TOC measurements have several significant limitations. Current devices are relatively slow, taking 120 seconds or more for each measurement. These devices usually require relatively large sample volumes and may require complex sample handling procedures. Current TOC instrumentation is often bulky and unsuitable for portable, on-line applications.

U.S. Pat. No. 3,958,941 of Regan describes a TOC measurement device which employs UV radiation to oxidize organic carbon species in a sample to $CO_2$. The $CO_2$ generated is then transported into pure deionized water and the change in conductivity of the deionized water due to added $CO_2$ is measured. In the Regan method, the sample is mixed with air prior to irradiation to facilitate oxidation of organics. The $CO_2$ generated by oxidation in the sample is transported into the deionized water by an air-stripping system. The method is not sufficiently rapid to allow continuous real-time measurement and requires relatively large sample sizes for accurate measurement. Other methods reported for measurement of TOC in water using conductivity measurements include U.S. Pat. No. 3,224,837 of Moyat, U.S. Pat. No. 4,293,522 of Winkler and more recently U.S. Pat. Nos. 4,626,413, 4,666,860, 4,868,127 of Blades and Godec, and PCT applications WO 94/35498 (Sievers Instruments) and WO 96/01999 (Millepore).

U.S. Pat. No. 4,277,438 of Ejzak reports a TOC measurement device in which air and an oxidizing agent are added to the sample prior to UV irradiation and in which the $CO_2$ generated from oxidation of organics is passed into a gas stream for IR analysis. U.S. Pat. No. 4,619,902 of Bernard also relates to a TOC measurement device using IR detection for $CO_2$.

The Blades and Godec patents supra all relate to a device and method for conductivity measurement of TOC in water using a single sample cell having two electrodes which can be exposed to UV radiation. Background conductivity is measured in the sample before exposure to UV light. When the UV light is switched on, conductivity is measured as a function of time and the second time derivative of the conductivity signal is measured to determine when oxidation is complete. Computer methods are applied to separate out signal due to background conductivity and obtain a measurement of TOC. Complete oxidation of organics in the sample is said to require variously 1–5 min. or 1–20 min. U.S. Pat. No. 4,666,860 further reports a method for prediction of TOC in a given sample based on measurement of conductivity at times before complete oxidation of organics has been achieved. This method requires initial calibration of the device using conductivity measurements over time for complete oxidation of a similar sample. It appears that this method is not useful for measurements where TOC may vary significantly from sample to sample. U.S. Pat. No. 4,868,127 further reports the use of a thin layer of $TiO_2$ formed on the titanium electrodes as an oxidation catalyst and the use of electrophoresis to accelerate reaction.

WO 96/01999 reports methods for rapid determination of TOC in water samples using conductivity measurements. TOC determinations in these methods are, however, predictions based on extrapolation from conductivity measurements at partial oxidation of the organics in a given sample.

Microfluidic devices have been employed for liquid phase analytical applications. U.S. Pat. No. 5,637,469 of Wilding et al. discloses microfabricated devices having a mesoscale flow system for the detection of analytes. Analyte detection is based on the binding of analyte to binding moieties within microfabricated channels in the flow system. Microfluidic devices do not appear to have been employed for the measurement of TOC in water samples.

The present invention represents a significant improvement over the prior art for measurement of TOC of water samples. The microfluidic TOC analysis device of this invention provides rapid measurement, not prediction, of TOC by measurement of conductance in water samples in which the organic carbon is substantially oxidized to $CO_2$ in times less than about 30 sec. The devices of the present invention provide accurate and reliable TOC measurements requiring relatively small sample volumes (30 µL or less). The use of small sample size increases sampling speed and decreases the time between measurements. The relatively small sample cells of this invention can be configured in a compact device suitable for portable instruments. The relatively small size of the sample cells and attendant detectors facilitate use of the TOC measurement devices of this invention in on-line applications.

SUMMARY OF THE INVENTION

This invention provides devices and methods for rapid real-time measurement of total organic carbon (TOC) in water. The invention is at least in part based on very rapid, substantially complete mineralization of organics in a water sample by UV irradiation. The irradiated sample is contained in a relatively thin light path sample volume to facilitate rapid mineralization. TOC of the water sample is determined by the detection of the $CO_2$ generated. The microfluidic sample cell of the TOC device of this invention is preferably configured to provide for irradiation of a relatively thin layer of sample to provide very rapid mineralization and to minimize the time required for making a TOC measurement. The method allows direct measurement of TOC of a given sample in a time shorter than about 30 seconds and more preferably provides for sufficiently rapid substantial mineralization (about 2 seconds or less) to allow real-time TOC measurements. The devices of this invention also facilitate minimal lag time between TOC measurement to allow fast, continuous measurements of TOC.

More specifically, this invention provides a device for measurement of TOC in water samples that employs a microfluidic sample cell. As used herein the term microfluidic refers to a sample cell with a sample channel, sample cavity or sample volume having at least one-dimension that is less than about 150 µm. Devices of this invention may employ static or stop-flow sample cells or flow cells. A source of UV radiation is provided for decomposition of organics in a sample within a sample channel, sample cavity or sample volume of the microfluidic sample cell. The sample cell is, at least in part, transparent to UV radiation such that a sample therein can be irradiated to decompose organics to $CO_2$. The sample volume exposed to radiation has a sufficiently thin irradiation path, less than about 150 µm, such that substantially complete mineralization of organics in the irradiated sample volume can occur within about 30 seconds or less, preferably in about 10 seconds or less and more preferably within about 2 seconds or less. The speed of mineralization of a given sample in a microfluidic sample cell will generally also depend upon UV light intensity in the sample volume and the concentration of organics in the sample.

The sample cell of the TOC measurement devices of this invention is optionally provided with a catalyst for enhancing decomposition of $CO_2$ on irradiation. This catalyst can be a photocatalyst, e.g., a photocatalyst that can generate oxidizing agents, such as superoxide and hydroxide radicals, in contact with the sample volume. A preferred photocatalyst is $TiO_2$, and a more preferred photocatalyst is platinized $TiO_2$. Oxygen or other oxidizing agents (e.g., persulfate) can also be introduced into the sample volume to facilitate mineralization of organics.

In the devices of this invention, a UV source is positioned to irradiate a sample volume in the sample cell. If present, the photocatalyst is positioned in contact with the sample volume and positioned to be irradiated by the UV source. Typically, in the device, a UV source is held in a fixed position with respect to the sample cell, for example, in a sample holder. The UV source may be in contact with the sample cell. A reflective surface or mirror can also be provided in the device, e.g., at the bottom of the sample cell, sample channel or sample cavity, to provide for multiple passes of light through the sample volume to increase the optical path length through the sample.

Optionally, an $N_2$ atmosphere or other non-UV-absorbing atmosphere is provided in any space or gap between the UV source and the sample cell. The device is provided with appropriate fluid connections, and/or valves and can be provided with or attached to a fluid pump in order to introduce water samples into or to expel water samples from the sample cell. Alternatively, in on-line configurations, pressure from a water or process line being sampled can be used to introduce and/or expel samples.

TOC measurement devices of this invention are provided with a detector for the $CO_2$ generated on irradiation of organics. A variety of detection methods, including various conductivity methods, infrared and related spectroscopic methods, can be employed. In one embodiment of this invention, $CO_2$ generated by UV irradiation of organics is detected using conductivity measurements. In a second embodiment of this invention $CO_2$ is measured by infrared spectroscopy, preferably nondispersive infrared spectroscopy (NDIR).

In a device of this invention for measurement of TOC using conductivity detection and quantitation of $CO_2$, the sample cell comprises conductivity electrodes in contact with the irradiated sample volume. The sample cell is also provided with a temperature sensing device (preferably in proximity to the conductivity electrodes) or a temperature control device to allow temperature compensation of conductivity measurements. The device is provided with appropriate electrical connections and attendant resistance meters or other output devices for measurement of conductivity and temperature. The temperature of the sample cells, preferably in proximity to the conductivity electrodes, is measured and/or controlled to allow for temperature compensation of conductivity measurements.

In a device of this invention for measurement of TOC using NDIR detection, conductivity electrodes and temperature sensing and/or control are not required. $CO_2$ generated on mineralization is transported or carried to the NDIR detector. The sample can be vaporized in the sample cell by heat generated by UV irradiation or by external heating, alternatively or in addition the sample may be vaporized after mineralization. A heated conduit for transport to the detector is used to avoid condensation on route. Standard NDIR detection methods appropriate for detection of $CO_2$ in the presence of water can be employed.

The TOC devices of this invention can have multiple path sample cells to allow compensation for background conductivity, $CO_2$ or other potential interferants in a non-irradiated control water sample. Multiple path sample cells can also be employed to make comparative TOC measurements of two or more water samples. The surface area of a sample volume exposed to UV irradiation can be varied by selecting the shape of the sample channel with a wider channel providing for a larger exposed surface area than a narrower channel. Similarly, a circuitous or meandering-path channel can be employed to provide for a larger exposed surface area than a simple straight channel. In a flow sample cell configuration, the sample flow rate and the length of channel path irradiated can be varied to adjust the UJV exposure time of a sample passing through the flow cell.

In a device of this invention for measurement of TOC using NDIR spectroscopy for detection and quantitation of $CO_2$, the sample cell is preferably a flow cell.

In one embodiment, the sample cell is formed from two overlaid substrates. A sample channel or cavity for receiving a sample is provided in between the two substrates. This channel or cavity can be provided in one or both of the overlaid substrates (e.g., by etching, micromachining or like process) or it can be provided by a spacer having a cavity or channel intermediate between the two substrates. The substrates can be directly or indirectly bonded together, e.g., using anodic bonding. At least one of the substrates is at least partially transparent to UTV radiation to allow the sample volume to be irradiated. The optional photocatalyst can be provided as a layer in the sample cavity or channel in contact with the sample volume. The photocatalyst is preferably provided as a layer on a substrate surface positioned to be irradiated by the UV light source and in contact with the sample volume.

Water samples can be pretreated, e.g. partially purified, deionized or filtered, before introduction into the microfluidic sample cells of this invention to prevent fouling of the device, minimize background conductivity and/or remove possible interferants. Water samples can, for example, be passed through a filtering device before entering the TOC device to remove particulates and/or passed through an ionic exchange column to reduce background conductivity.

TOC measurement devices of this invention can be used for determination of water quality in supply lines, process lines and the like and can be directly linked on-line for continuous or periodic assessment of TOC. These devices can also be employed in combination with alarm or feedback control systems to detect the presence of an unacceptable TOC level in a water supply line to allow diversion of contaminates and/or prevent contamination of processes. Devices of this invention are particularly useful in applications in the semiconductor industry, particularly with respect to quality of water used in process or cleaning steps.

This invention provides methods for rapid measurement of TOC using the device configurations described hereinabove. Devices and methods of this invention do not rely on prediction of TOC based on partial oxidation of organics in water samples to achieve measurements in less than about 30 sec. However, art-known methods of predicting TOC based on partial oxidation of samples can be coupled to the improved speed of actual measurements provided by the devices of this invention to even further improve the speed of measurements. It is understood that application of such predictive methods can, however, introduce measurement error leading to decreased accuracy of TOC measurements.

DETAILED DESCRIPTION OF THE INVENTION

Figure 1A:
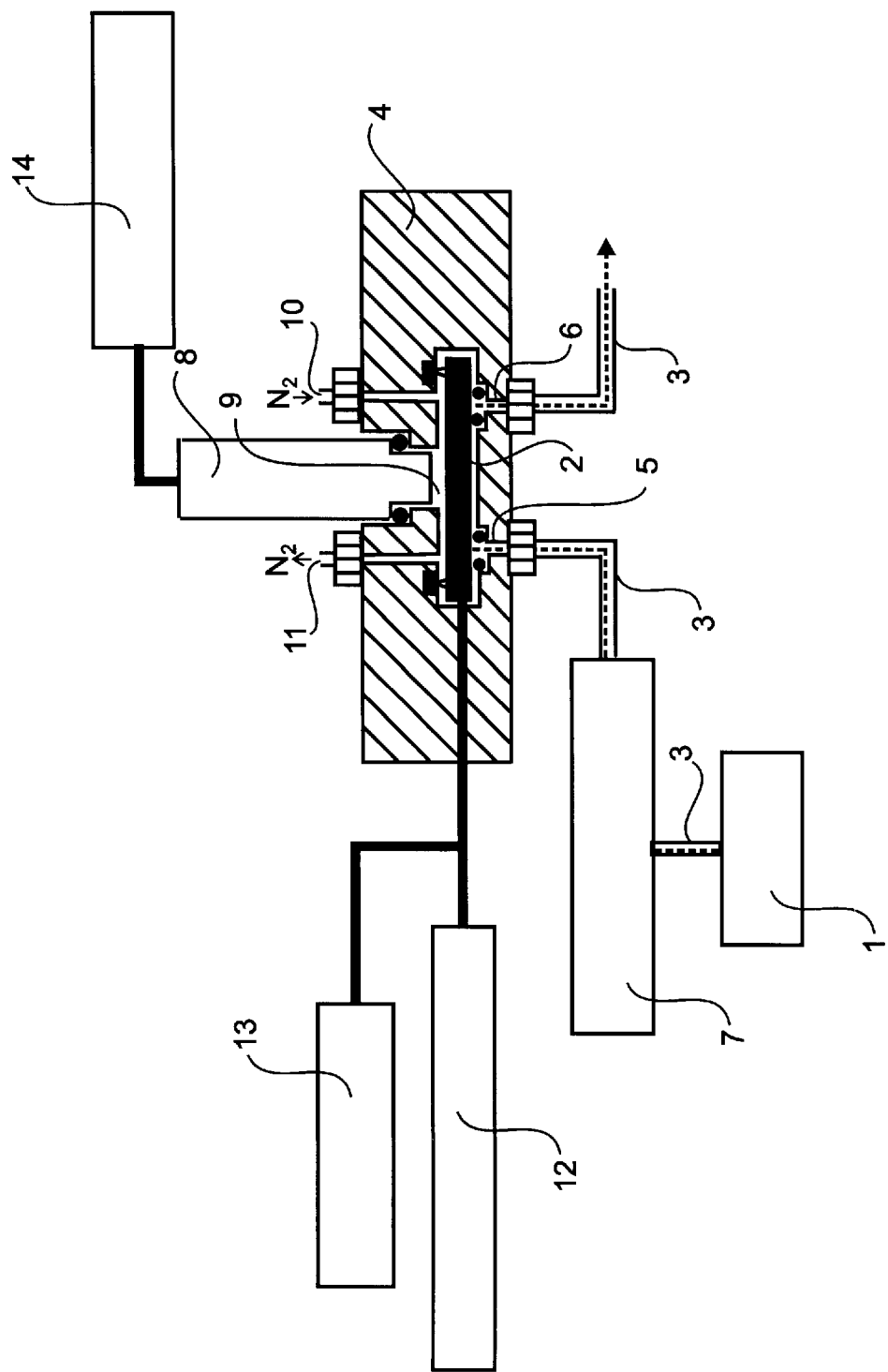
FIG. 1A is a schematic drawing of a TOC device of this invention for conductivity detection of $CO_2$ generated on mineralization of organics in a water sample.

The following terms are defined for use herein:

"Microfluidic" as applied to the terms sample cell and TOC device refers to a TOC device having a sample cell containing a sample channel, sample cavity or sample volume, in which one of the dimensions of at least a portion of the sample channel, cavity or volume is smaller than about 150 µm. More specifically, sample cells of this invention include sample channels (cavities or volumes) that are less than about 150 µm thick within the portion of the channel in which the sample is subjected to irradiation to mineralize organics to $CO_2$. The sample being irradiated is thereby confined to a relatively thin layer, preferably perpendicular to the direction of the irradiating light and whose thickness is preferably less than about 150 µm, to facilitate rapid oxidation and mineralization of organics in the water sample.

"Mineralization" refers to the oxidation of organics present in water sample to $CO_2$. The concentration of $CO_2$ in the water after mineralization is measured to determine TOC. To obtain the most accurate results, the organics in a sample should be completely mineralized, i.e. all organics present should be oxidized to $CO_2$. Water samples may, however, from time to time contain organic species that are hard to oxidize. Most often it is expected that the amount of such oxidation resistant organic materials will be very low. Dependent upon the particular application of the TOC device of this invention, "substantial mineralization" or "substantially complete oxidization," in which a residue of such hard to oxidize organics may still be present, can be sufficient to obtain a TOC measurement of desired accuracy.

The device configurations of this invention provide for rapid mineralization (oxidation) of organics to $CO_2$ using UV irradiation. Samples can be mineralized in 30 seconds or less and preferably in 10 seconds or less and more preferably in 2 seconds or less. The limiting step in a conductivity determination of a given sample in the sample channel is the time required for mineralization. The use of the microfluidic sample cells of this invention significantly decrease the time required for TOC conductivity measurements. Additional time is required for flushing samples from the static sample cell and introducing new samples. This lag time can be minimized by use of appropriate fluid handling systems to increase the speed of sequential TOC measurements. In a continuous flow sample cell, in which $CO_2$ concentration can be monitored continuously as a function of time, the sampling lag time is minimized to allow fast, continuous TOC measurement.

The rapid mineralization of water samples containing organics that can be achieved in the microfluidic devices of this invention allows for real-time measurement of TOC. The term "real-time" is used herein in a practical way to indicate that a measurement of TOC can be made sufficiently rapidly to allow an appropriate real-time response to the measurement. For example, a real-time measurement of TOC in the water in a process line would be sufficiently rapid to allow efficient and rapid diversion of any contaminated water to avoid process contamination. Real-time TOC measurements include those that can be made within less than about 10 seconds.

The invention is further illustrated in the following description in reference to the drawings in which like numerals are used to describe like features.

FIG. 1A is a schematic representation of a TOC device of this invention with a microfluidic sample cell 2. The sample cell 2 is held within a holder 4. The holder is furnished with fluid connectors, an inlet 5 and an outlet 6 for introduction and exit, respectively, of a sample. The direction of sample flow into and out of the cell is indicated in FIG. 1A. The device has a fluid handling system for carrying a sample from a water supply to be tested to the sample cell. This system includes fluid transport tubes or channels (3) and pump 7 (which may be a peristaltic pump) which facilitates sample flow in the system. The cell and its fluid handling system can be operated in a flow mode in which a sample continuously passes through the cell at a selected flow rate. Alternatively, the cell can be operated in a static or stop-flow mode in which a discrete sample is introduced into the cell and flow is stopped. The fluid handling system may be provided with one or more valves (not shown) to isolate the water supply (1) from the TOC device. In a continuous flow system, the fluid handling system can be provided with appropriate flow controllers or regulator (not shown). In an alternate fluid handling system with no pump, pressure from the water supply line is employed to introduce and later expel sample from the sample cell. In this case, inlet and outlet valves would be provided in the fluid transport channels. The pump (7) is shown in the fluid handling system upstream (with respect to water flow) from the sample cell. The pump can alternatively be positioned downstream of the sample cell functioning by pulling fluid through the system.

UV source 8 is positioned and held in holder 4 adjacent the sample cell to irradiate at least a portion of a sample channel 20 (FIG. 1B) in the sample cell. Power supply 14 provides power to the UV source. The sample cell is sealed within the sample holder, the UV source is introduced into the holder and a seal is formed between the source and the holder forming a sealed space or gap 9 between the cell and the UV source. This space may be filled with a gas (via gas conduits 10 and 11) that does not absorb in the UV, such as $N_2$, to expel $O_2$ which absorbs in the UV.

Figure 1B:
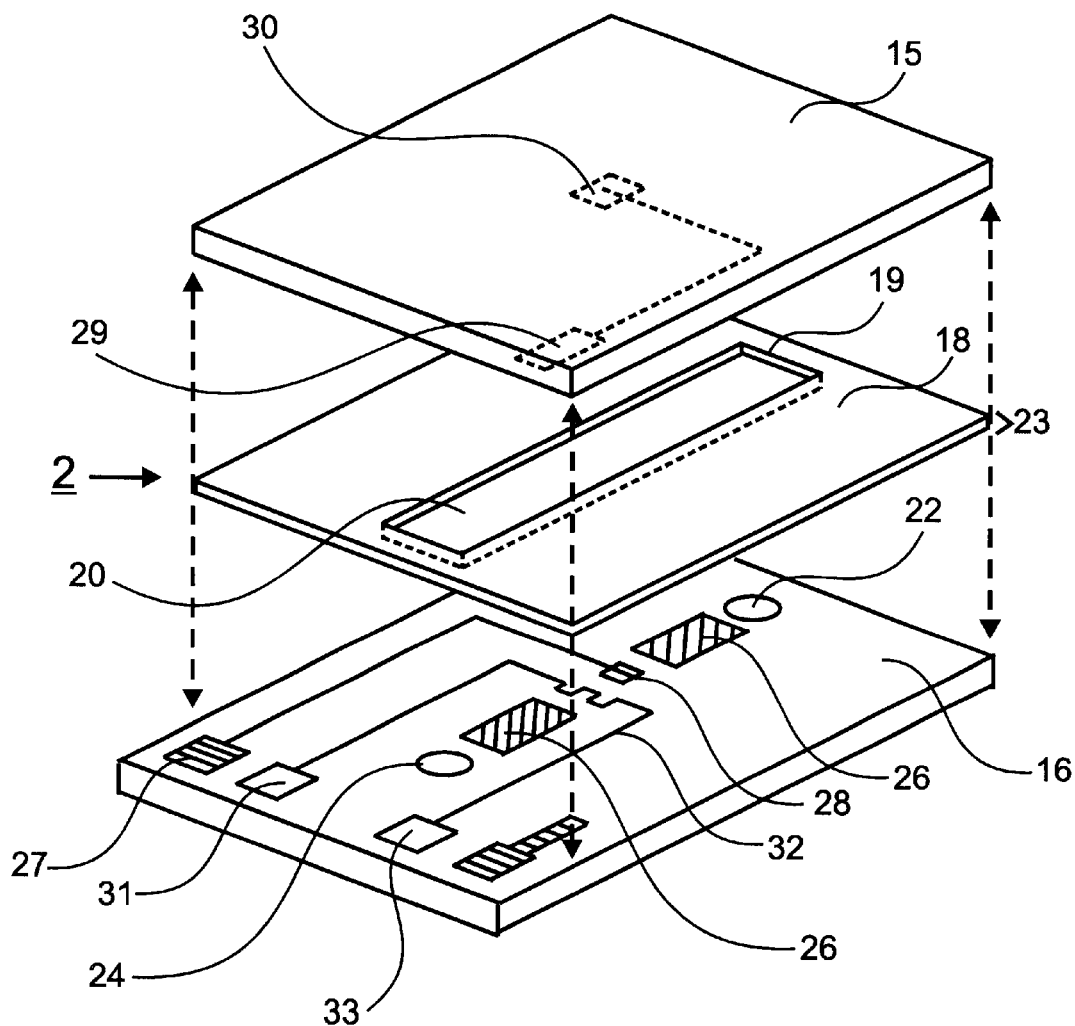
FIG. 1B is an enlarged, exploded schematic drawing of a microfluidic sample cell of this invention.

The device of FIG. 1A is configured for conductivity detection of $CO_2$ employing conductivity meter 12 which is electrically connected to conductivity electrodes (28, 30) in the sample cell (FIG. 1B). A resistive temperature sensor (32, FIG. 1B) is provided in the sample cell employing resistance meter 13 which is electrically connected to a resistive temperature sensor in the sample cell (FIG. 1B).

FIG. 1B is an enlarged, exploded illustration of sample cell 2. The cell is formed between two substrates: Top substrate 15 and bottom substrate 16. (The terms top and bottom are used in figures herein in reference to the irradiating UV source; the top substrate is the substrate closest to the lamp; UV radiation enters the cell through the top substrate.) The top substrate is at least partially transparent to UV radiation. Membrane spacer 18, having shaped cavity 19 is inserted between the substrates to form sample channel (or sample cavity) 20. The thickness of the sample channel (23) is determined by spacer thickness. The sample volume is the sample contained within the sample channel or cavity some or all of which volume may be irradiated. Two holes into the sample channel, shown in FIG. 1B as passing through the bottom substrate, provide a sample inlet 22 and outlet 24 connected via fluid inlet and fluid outlet 6, respectively, to the fluid handling system of FIG. 1A. One or more photocatalyst elements 26 are optionally provided within the sample channel in contact with the sample volume. This element is shown as a deposited layer on the inner surface of the bottom substrate 16 in FIG. 1B.

Conductivity electrodes 28 and 30 are positioned within the sample channel in contact with the sample volume. These electrodes are illustrated as formed on the topside of bottom (16) and underside of the top (15) substrates of the cell, respectively, spaced apart by the sample channel and sample volume thickness in FIG. 1B. A resistive temperature sensor 32 is positioned within sample channel 20 in contact with the sample volume. Electrical connections 27 and 29 allow for connection of the conductivity electrodes to the conductivity meter (12 in FIG. 1A). Electrical connections 31 and 33 allow for connection of the temperature sensor to resistance meter 13 (FIG. 1A).

In operation in the static or stop-flow configuration, a sample is introduced into the sample channel and a measurement of background conductivity is made. The sample is irradiated with the UV source and conductivity of the irradiated sample is followed to detect $CO_2$ as a function of time. TOC is determined from the maximum value for $CO_2$ generated.

Figure 1C:
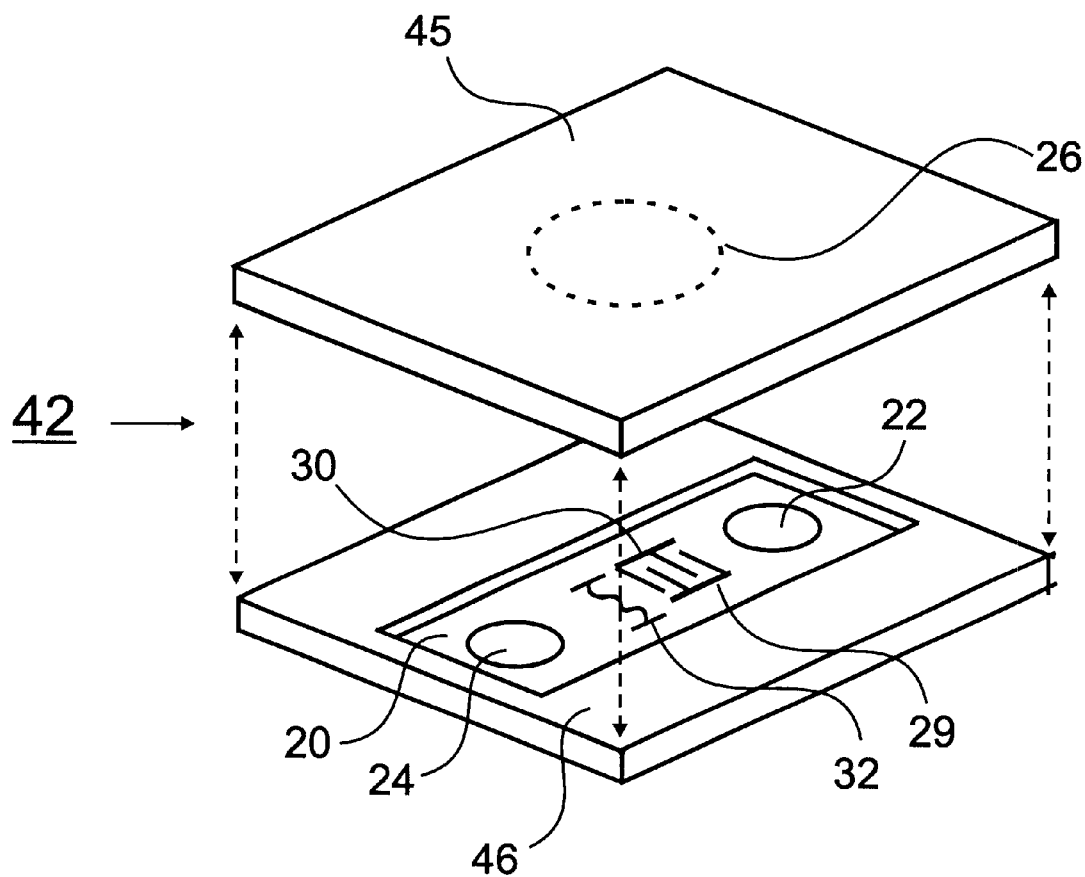
FIG. 1C is an enlarged, exploded schematic drawing of an alternate microfluidic sample cell of this invention.

FIG. 1C is a schematic exploded illustration of another microfluidic sample cell (42) of this invention. This cell is also configured for conductivity measurement of TOC. The sample cell is formed from a fused silica top substrate 45 and a silicon bottom substrate 46. Sample channel (sample cavity) 20 is provided by micromachining a cavity into the silicon bottom substrate. Sample inlet and outlet holes 22 and 24, respectively, are also micromachined into the bottom substrate 46. The sample channel 20 is formed by anodically bonding the top substrate to the micromachined bottom substrate. Top substrate 45 is at least partially transparent to UV irradiation to allow the sample volume (or a portion of the sample volume) to be irradiated. The cell is optionally provided with a photocatalyst element 26, shown in this figure as a layer on the inner surface of the top substrate in contact with the sample volume. Conductivity electrodes 28 and 30 are positioned in the sample channel in proximity to the irradiated sample volume. The conductivity electrodes (28 and 30) are a shown as interdigital electrodes which are convenient for the configuration of FIG. 1C. A resistive temperature sensor 32 is provided in the sample cell, preferably in close proximity to the conductivity electrodes. Electrical connections for the temperature sensor and conductivity electrodes (not shown in FIG. 1C) can be made on the bottom of the silicon substrate using art-known techniques, for example vias.

Interdigital electrodes are deposited on the same substrate surface. These electrodes are more easily and less expensively prepared than parallel electrodes as in FIG. 1B. There is, for example, no need to carefully align the electrode faces as is required when using parallel electrodes on opposite substrate faces (see FIG. 1B). This type of electrode is also more easily mass produced. The device of FIG. 1C is operated in a similar manner to the device of FIG. 1B.

Figure 1D:
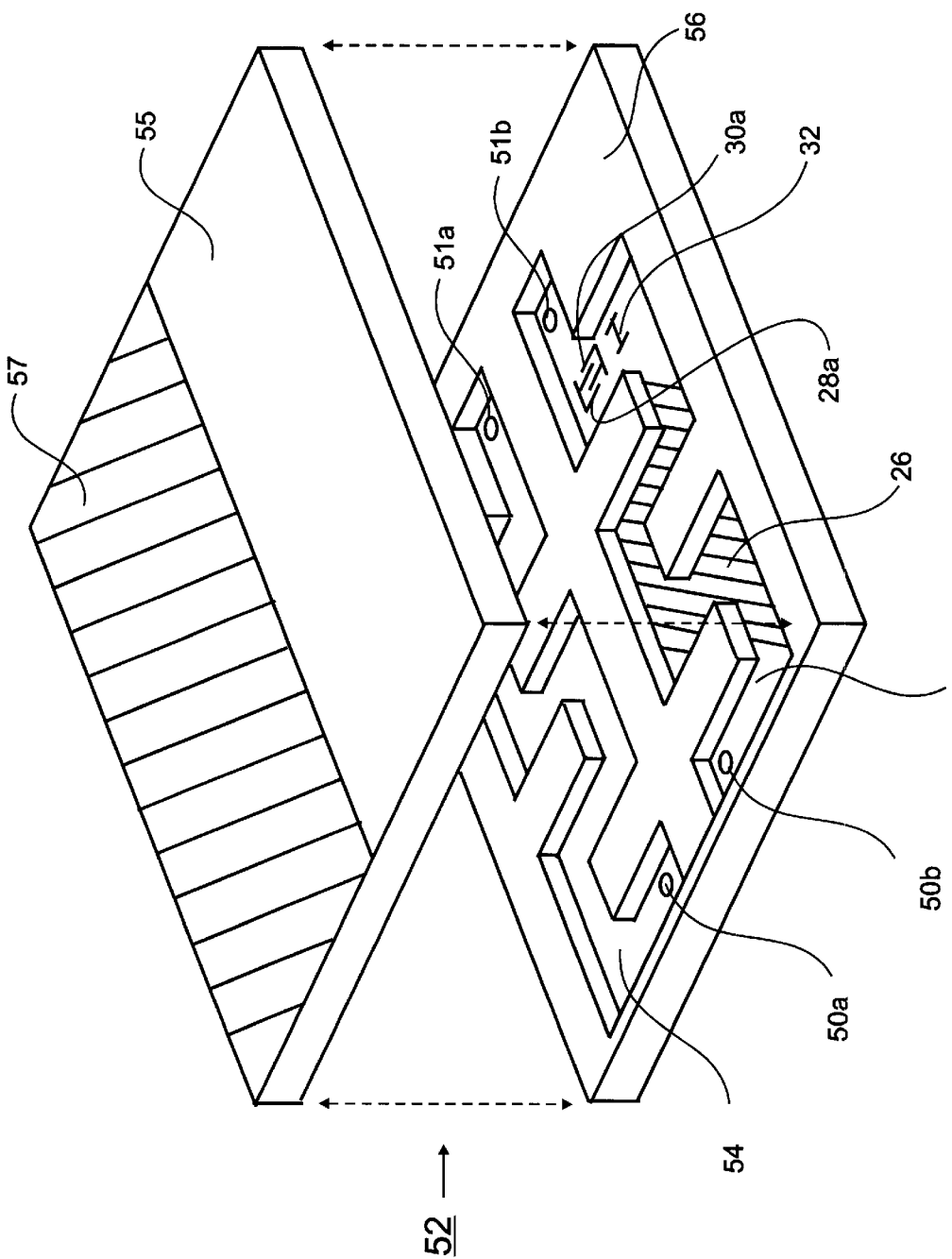
FIG. 1D is an enlarged, exploded schematic drawing of an alternate microfluidic sample cell of this invention configured for conductivity measurement of TOC in a flow cell design. The sample cell comprises two separate sample channels.

FIG. 1D is a schematic, exploded drawing of another microfluidic sample cell of this device. The sample is configured for flow cell operation and is provided with conductivity detection of $CO_2$. The sample cell of FIG. 1D is a two path, continuous flow microfluidic sample cell.

Sample cell 52 is formed from a top and a bottom substrate (55 and 56, respectively) the planar faces of which are bonded together. Two shaped cavities 53 and 54 are formed in the bottom substrate, by micromachining and/or etching processes. These cavities form two sample channels when the sample cell is formed. Each channel has an inlet (50a and 50b) and an outlet (51a and 51b) hole at either end of their respective channels for sample transport. These holes can be micromachined or etched into the bottom substrate. The channel, with its inlet and outlet provide a sample flow path through the sample cell. The channels are illustrated as having a circuitous or meandering path (e.g., not a straight-line path). One of the sample channels can be used as a control channel and the other can be used as a measurement channel, for example. The top substrate 55 is at least partially transparent to UV irradiation. Preferably, a UV shield 57 is provided to prevent irradiation of the control channel. In FIG. 1D, sample channel 54 is illustrated as a non-irradiated control channel. Sample channel 53 is illustrated as a measurement channel which is irradiated. This sample measurement channel (53) is optionally provided with a photocatalyst element 26 which is illustrated as a layer in the measurement channel on the inner surface of the bottom substrate. A pair of conductivity electrodes (28a, 30a) is positioned in the measurement sample channel near the outlet hole (51b). A second pair of interdigital conductivity electrodes (not shown) is positioned in the control channel near the outlet (51a). One or two resistive temperature sensors 32 are also provided in the cell in the sample and control channel in close proximity to the conductivity electrodes. The electrodes and the temperature sensor are illustrated as patterned on the bottom substrate near the outlet hole of each channel. Electrical connections (not shown) can be provided on the back side of the bottom substrate using art-known techniques, including vias.

The flow cell of FIG. 1D can be made as illustrated in FIG. 1C by anodic bonding of a fused silica top substrate to a micromachined bottom silicon substrate. The two flow paths and inlet and outlet holes are provided by micromachining.

Figure 1E:
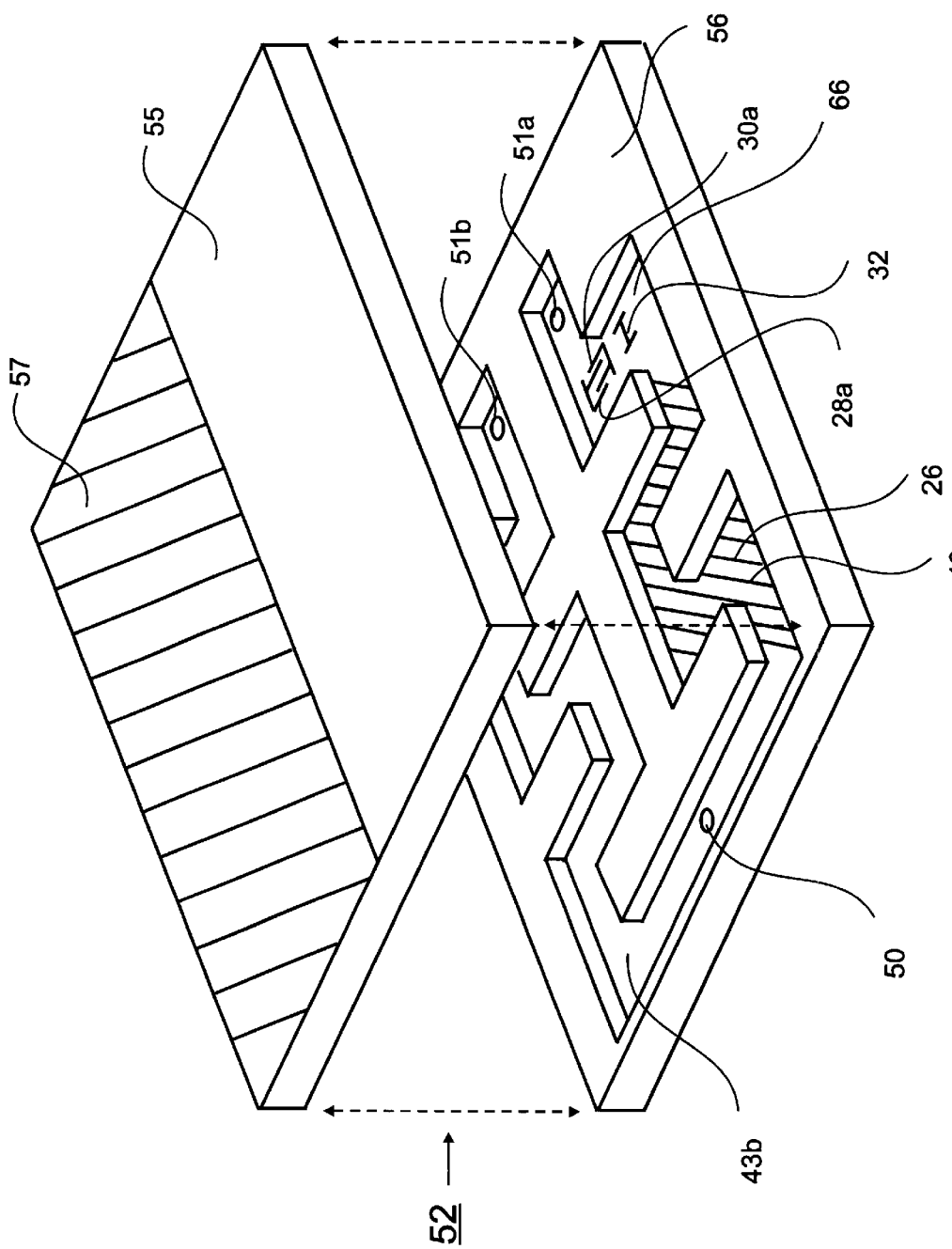
FIG. 1E is an enlarged, exploded schematic drawing of an alternative microfluidic sample cell of this invention configured for conductivity measurement of TOC in a flow cell design. The illustrated sample cell has two sample flow channels with a shared inlet.

FIG. 1E is another example of a microfluidic flow cell 52 for use in the TOC measurement devices of this invention. Sample cell 52 is formed from a top and a bottom substrate (55 and 56, respectively) the planar faces of which are bonded together. A shaped cavity 66 is formed in the bottom substrate, by micromachining and/or etching processes. When the sample cell is formed by bonding the top and bottom substrates, the shaped cavity forms two fluid channels 43a and 43b. One shared inlet hole 50 at the inlet end of the channels and two outlet holes (51a and 51b, one for each channel) at the outlet end of the channels are provided for sample transport. These holes can be micromachined or etched into the bottom substrate. The channels, with shared inlet and separate outlets provide two sample flow paths through the sample cell. The channel flow paths are illustrated as having a circuitous or meandering path (e.g., not a straight-line path). One of the sample flow channels can be used as a control channel and the other can be used as a measurement flow channel, for example. The top substrate 55 is at least partially transparent to UV irradiation. Preferably, a UV shield (57) is provided to prevent irradiation of the control channel. In FIG. 1E, sample channel 43b is illustrated as a non-irradiated control channel. Sample channel 43a is illustrated as a measurement channel which is irradiated. This sample measurement flow channel (43a) is optionally provided with a photocatalyst element 26 which is illustrated as a layer in the measurement channel on the inner surface of the bottom substrate. A pair of interdigital conductivity electrodes (28a, 30a) is positioned in the measurement sample channel (43b) near the outlet hole. A second pair of conductivity electrodes (not shown) is positioned in the control channel near the outlet. One or two resistive temperature sensors 32 are also provided in the cell in the sample and control channels in close proximity to the conductivity electrodes. The electrodes and the temperature sensor are illustrated as patterned on the bottom substrate near the outlet hole of each channel. Electrical connections (not shown) can be provided on the back side of the bottom substrate using art-known techniques, including vias.

In a flow cell configuration for conductivity measurement of TOC, sample is introduced into each flow path of the sample cell of FIG. 1D or FIG. 1E at a selected flow rate. The sample in the measurement channel is irradiated to mineralize the organics therein to $CO_2$ as the sample flows through the cell. The sample in the control path is not irradiated. Conductivity is measured near the end of the flow path and a comparison is made between the sample in the measurement path and the sample in the control path to exclude background conductivity. The flow rate is adjusted preferably to insure substantially complete mineralization of the measurement sample before it reaches the conductivity electrodes.

Sample cells analogous to those illustrated in FIGS. 1D and 1E can have a plurality of separate sample channels for comparison of different water samples.

Figure 1F:
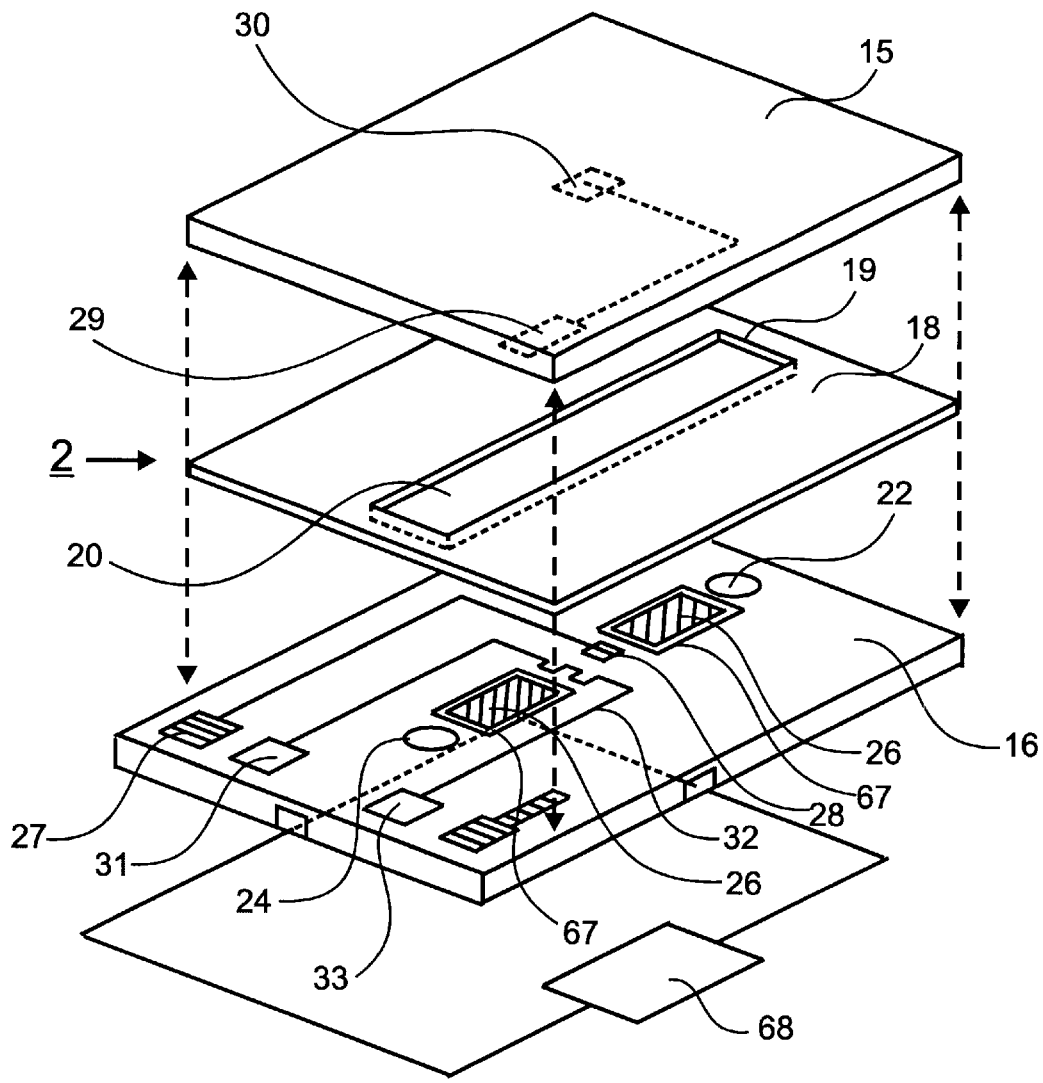
FIG. 1F is an enlarged, exploded schematic drawing of an alternative microfluidic sample cell of this invention configured for photoelectrocatalysis with a counterelectrode positioned with respect to the photocatalyst layer to allow a bias voltage to be applied to the photocatalyst layer.
Figure 1G:
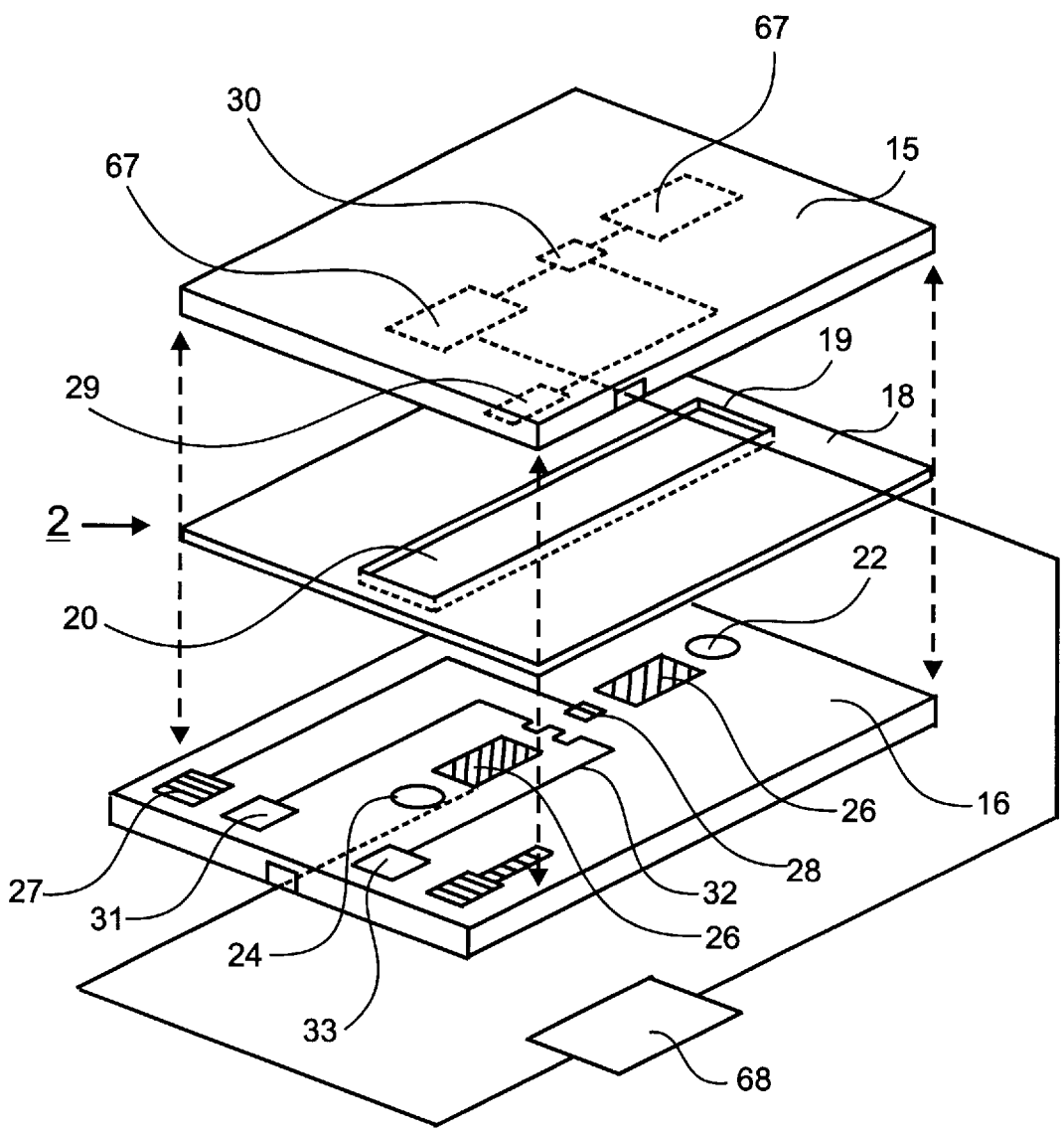
FIG. 1G is an enlarged exploded drawing of an alternative sample cell of this invention having a counterelectrode positioned on the underside of the top substrate adjacent the photocatalyst layer to allow application of a bias voltage to facilitate photoelectrocatalysis.

FIGS. 1F and 1G illustrate exemplary positioning of counterelectrodes with respect to a $TiO_2$ photocatalyst electrode. In FIG. 1F a counterelectrode 67 is deposited on the bottom substrate around the photocatalyst film 26. Electrical connections to a power supply 68 (e.g., DC power supply) are provided through the bottom substrate. A bias voltage (0–2 volts) can be applied between the photocatalyst film (preferably a $TiO_2$ film) and a counterelectrode (e.g., Ti or Zr thin-film) to enhance photocatalysis.

FIG. 1G illustrates an alternative position for the photocatalyst layer counterelectrode 67 as a layer deposited on the underside of the top substrate (15). The counterelectrode should be positioned with respect to the photocatalyst layer to minimize blockage of UV irradiation. For example, electrodes that are transparent or semi-transparent can be employed, the size and shape of the counterelectrode can be adjusted, or the direction or angle or irradiation can be adjusted to allow for maximum photocatalyst irradiation. Electrical connections to a power supply 68 are provided.

Figure 2A:
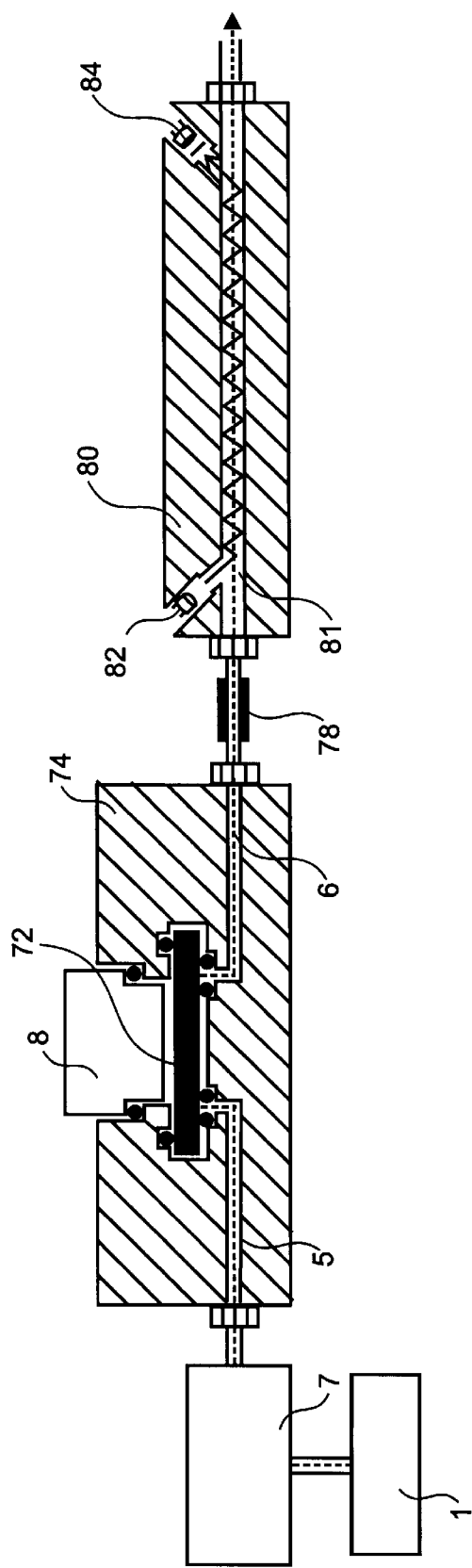
FIG. 2A is a schematic drawing of a TOC device of this invention for infrared detection of $CO_2$ generated on mineralization of organics in a water sample. The device is illustrated with an NDIR detector.

FIG. 2A is a schematic illustration of a microfluidic TOC analysis device employing an NDIR detector for quantitation of $CO_2$. The device provides for continuous monitoring of trace levels of organic contaminants. The device has a sample cell 72 and a UV source 8 both positioned within holder 74. The UV source can be spaced away from the sample cell and the space between can be filled with a non-UV-absorbing gas, such as $N_2$. A fluid handling system is provided for introducing a sample from a water supply to the sample cell. The fluid handling system includes an inlet 5 to the sample cell, pump 7 and connecting fluid tubing. The device includes NDIR detector 80 connected to the sample cell via a heated column 78. The NDIR detector has a multiple reflection gaseous sample chamber 81 with an infrared source 82 for introducing IR radiation into the sample chamber and an infra red detector 84 for detection of absorption of infrared radiation by a gaseous sample in chamber 81. A water sample introduced into the sample cell is irradiated with UV to mineralize organic carbon generating $CO_2$. The sample containing $CO_2$ exits the sample cell, is vaporized and introduced into the NDIR detector chamber where the amount of $CO_2$ generated from organic carbon is specifically measured by detection of infrared absorption by $CO_2$. Vaporization of the sample can occur (at temperatures over about 100° C.) during mineralization with heating provided by UV irradiation or by heating of the cell.

Figure 2B:
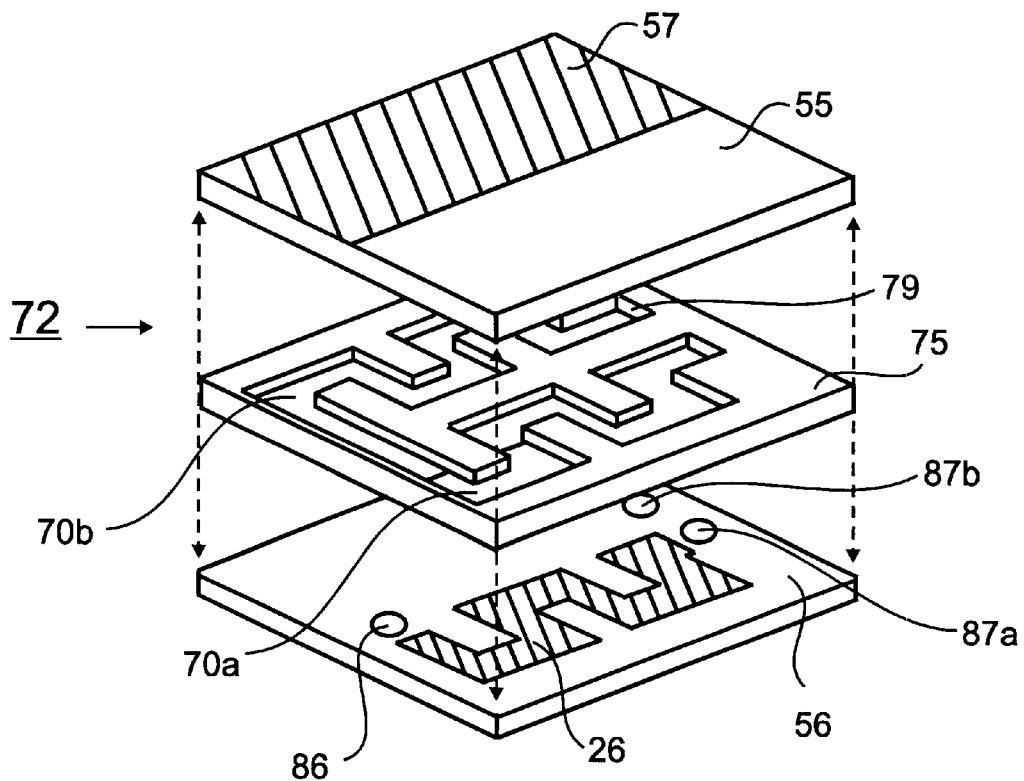
FIG. 2B is an enlarged, exploded schematic drawing of a microfluidic sample cell of this invention for mineralization of organics in a water sample.

FIG. 2B is a schematic of a microfluidic sample cell 72 for mineralization of organic carbon in a water sample. The cell is formed by overlaying two substrates: a top substrate 55 and a bottom substrate 56. Membrane 75 with shaped cavity 79 is inserted between the two substrates to form a two path channel 70a and 70b when the sample cell is formed by bonding of the membrane between the top and bottom substrates. A sample inlet 86 and two outlets 87a and 87b are provided as holes in the bottom substrate. Cavity 79 is shaped and the inlet and outlet holes are positioned within the sample volume to create two sample paths: one 70a, a measurement path, which can be irradiated with UV light and the second, a control path, 70b which is shielded from UV irradiation. Shielding 57 can be provided as illustrated by coating a portion of the top substrate with a UV filter. A photocatalytic element 26 is optionally provided in the irradiated sample path 70a. The outlet from the irradiated sample path 87a is connected to the NDIR detector via heated column 78. The outer side of the bottom substrate is optionally mirrored to facilitate multiple passes of UW radiation through the irradiated sample and any photocatalytic layer present.

The detection strategy in the device of FIG. 2A relies on vaporizing a sample in which the organics have been mineralized and determining the concentration of $CO_2$ generated in a given sample by infrared absorption. The preferred IR detector is an NDIR spectrometer which combines high sensitivity, fast response time, low noise levels and compact size. Design and operation of NDIR spectrometers are well-known in the art. For the present application, a heated NiCr wire is the preferred infrared source and a thin-film thermopile is the preferred infrared detector. It may be necessary to cool the detector to achieve the desired levels of $CO_2$ sensitivity (less than about 5–10 ppm). Thermopile detectors are well-known in the art and commonly employed as detectors in NDIR spectrometers. Thermopile detectors convert radiant energy into heat that is sensed over a wide spectral range. In the present application, filters can be employed to isolate, and allow selective detection of, IR wavelengths absorbed by $CO_2$.

Figure 2C:
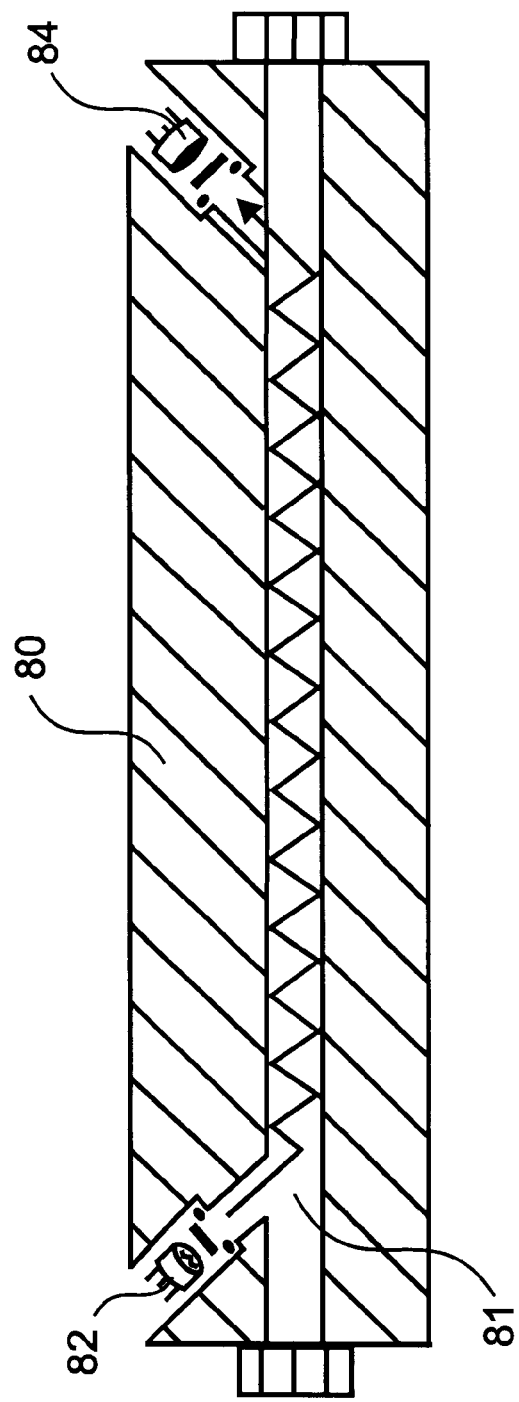
FIG. 2C is a schematic drawing of an NDIR detector useful in TOC devices of this invention.

A differential NDIR detector 80 is shown in more detail in FIG. 2C. The detector is operated at a sufficiently high temperature to avoid sample condensation, e.g., 110° C. A long path length gas cell having a multiple reflection design 81 is used to achieve a very high pathlength to volume ratio. The infrared source 92 and the infrared detector are separated from the gas sample cell by sapphire windows 97 using gas-tight seals (e.g., ethylene propylene O-ring seals). Sapphire is inert and transmits over 80% of the infrared energy over wavelengths ranging between 200 nm to 5 $\mu$m. $CO_2$ absorbs infrared radiation around 4 $\mu$m. The NDIR detector can be calibrated, if necessary or desired, employing an FTIR spectrometer with known $CO_2$ standards.

In preferred embodiments the substrates employed for microfluidic sample cells of this invention are fused silica plates or silicon wafers. Fused silica materials offer superior transmittance down into the far UV. Over 92% of incident UV energy is transmitted by fused silica over wavelengths ranging between 170 to 400 nm. The sample channel in the sample cell is preferably formed between two substrates. The sample channel is preferably formed by etching or micromachining a cavity or cavities on the inner face of the substrates. This method is particularly useful for preparation of very thin cavities. In these embodiments, the substrates can be directly bonded together, for example, by anodic bonding.

Alternatively, the sample channel can result from a cavity formed by insertion of a thin membrane having a cavity between the two substrates. The shape of the sample volume and its thickness is determined by the pattern of the cavity in the membrane and the thickness of the membrane, respectively. Any membrane material employed should be resistant to a variety of chemicals and solvents and resistant to moisture, resistant to UV radiation, have low permeability to vapor and gases, and have a wide useable temperature range. Further, it is useful that the membrane material is an electrical insulator, has good mechanical strength and bond strength to silica, is melt-processable and exhibits low creep and cold flow. Preferred membrane materials are fluorocarbon thermoplastics, particularly chlorotrifluoroethylene (McMaster-Carr, Chicago, Ill.). When using a thermoplastic membrane the sample cell can be formed by machining a cavity in the membrane, sandwiching the membrane between the top and bottom substrates, and heating the entire cell briefly followed by cooling to form a seal between the layers. Brief heating to about 250° C. followed by cooling to room temperature facilitates bonding of cells using a chlorotrifluoroethylene membrane. Sample volumes can be prepared by a combination of substrate etching and the use of intermediate membranes. Fused silica substrates can also be sealed together using sodium silicate or spin-on-glass bonding, both of which are known in the art.

Sample channels are preferably 150 μm or less thick where the sample is being irradiated to facilitate rapid mineralization of organics in samples. Sample cells can have a single sample flow path with one inlet and one outlet. Sample cells can have more complex designs with multiple flow paths entering the cell from a single sample inlet, following separate flow paths and exiting at separate multiple sample outlets. The flow paths created by shaping of the sample volume and placement of inlets and outlets can be direct or circuitous (meandering) as desired. Cells designed to operate in a flow sample mode preferably have more circuitous sample paths to provide a longer exposure of the sample to UV radiation. The sample flow rate, UV intensity and flow path while irradiated, are preferably adjusted to obtain substantially complete mineralization of organics in the irradiated sample before the sample exits the flow channel.

Conductivity electrodes of this invention can be microelectrodes fabricated on the inner surface of substrates (on one or both substrates). Photolithography or related surface patterning techniques can be used to fabricate electrodes. The electrodes in FIG. 1B are illustrated as aligned in a parallel plate geometry with an electrode on both the top and bottom substrate. Electrical connection to the electrode 29 on the top substrate is made by placing a small amount of conducting epoxy between the end of electrode 37 and bond pad 35. The bottom substrate is slightly longer than the top substrate to facilitate electrical connection to 27, 29, 31 and 33. The electrodes in FIG. 1C are illustrated as interdigital electrodes on one substrate surface. In this case, electrical connections to the electrodes can be made through the substrate using vias or related techniques.

The specific design and geometry of the electrodes in the sample cell determines the conductivity cell constant. In a parallel plate electrode (two parallel electrodes) design the cell constant is the distance between the plates divided by the area of the plate. For more complex electrode geometries, the cell constant can be determined empirically by measurement of conductivities of standard solutions of known concentrations of ions. In a given conductivity application, the cell constant is generally selected to provide the desired level of sensitivity along with ease and simplicity of the measurement electronics. Preferred conductivity electrodes designs for use in devices of this invention have cell constants of 0.1 or less.

An overview of analytical conductometry is provided by J. W. Loveland, "Conductometry and Oscillometry" in *Treatise on Analytical Chemistry. Part I. Theory and Practice*, Chapter 51, John Wiley and Sons, New York (1963).

Inlet and outlet holes in substrates can be formed by drilling, for example using a diamond tipped drill unit, or more preferably by micromachining or etching techniques.

A light source is used in the TOC devices of this invention to decompose and mineralize (to $CO_2$) organics in water samples. Photodecomposition requires the presence of oxygen and/or other oxidizing agents in the sample. For typical analyses of pure water samples, ambient levels of oxygen present in the water sample should be sufficient for oxidation of organics present. However, oxygen and or other oxidizing agents, including ozone, can be introduced into the sample being irradiated. Photocatalyst, as detailed below can also be employed to generate oxidizing agents, e.g., $O_2^-$ or OH radicals, for example, without the presence of $O_2$, ($O_2^-$ and OH radicals can be produced from $H_2O$), and speed up oxidation. The amount of $CO_2$ generated is detected to determine the amount of total organics present in a given water sample.

UV sources are generally preferred for use in the devices of this invention. The term UV is used generically herein to encompass both far and near UV light. Far UV, wavelengths from about 180 to 260 nm, are preferred for decomposition of organics in the absence of photocatalysts. UV sources are also generally preferred for use with photocatalysts. However, the preferred wavelengths for use with a given photocatalyst depends upon the bandgap of the catalyst. A UV source for general use in the devices of this invention preferably produces intense continuous radiation at wavelengths less than about 400 nm. It is appreciated in the art that such sources may vary in intensity as a function of wavelength over this region. The UV source is preferably selected to provide radiation at wavelengths that effect most efficient oxidation of organic carbon in the samples. This choice will depend, at least in part, upon whether or not a photocatalyst is present, the nature of the photocatalyst and the bandgap energy of the photocatalyst. The UV source or other light source is preferably positioned adjacent the top substrate as close to the substrate and cell as possible to enhance light intensity at the sample, but allowing sufficient spacing to avoid overheating of the source or damage to the sample cell or holder. The UV source and the sample cell may be cooled or temperature controlled using a feedback mechanism coupled, for example to a thermoelectric heater/cooler.

In general a variety of UV light sources can be employed. More intense light sources being preferred. A UV light source useful in the devices exemplified herein is a rare-gas lamp which produces radiation between about 250 to about 600 nm. An exemplified preferred UV sources are rare-gas capillary and grid lamps, e.g. a Xe capillary lamp or a Xe grid lamp with intensities from about 9 to 18 $mW/cm^2$ at a distance of 19 mm, and from about 15 to 100 $mW/cm^2$ at 25 mm, respectively, from the source. Since UV intensity varies as $1/r^2$, where r is the distance from the source), significant intensity improvement can be achieved by decreasing the distance between the sample volume and the UV source. In exemplary devices of this invention, this distance has been successfully decreased to about 2 mm with Xe capillary sources without significant overheating or damage to device elements. Rapid complete mineralization of organic carbon (up to about 10 ppm) in water samples in 30 sec or less can be achieved using such intense UV sources in combination with thin (less than 150 μm) sample volumes.

A photocatalyst can be used to enhance efficiency or speed of oxidation of organics in water samples. Useful photocatalysts generate oxidizing agents in situ within the sample volume on irradiation with UV light. Photocatalysts useful in this invention include various chalcogenide semiconductors, including among others $TiO_2$, $WO_3$, $SnO_2$, ZnO, and CdS (N. Serpone et al. (1986) "Photocatalysis over $TiO_2$ supported on a glass substrate" Solar Energy Materials 14:121–127; M. Gratzel (ed.) (1983) *Energy Resources through Photochemistry and Catalysis*, Academic Press, New York, N.Y.; M. Schiavello (ed.) (1985) *Photoelectrochemistry, Photocatalysis and Photoreactors*, D. Reidel, Dordrecht, Holland; E. Pelizzetti and N. Serpone (1986) *Homogeneous and Heterogeneous Photocatalysis* (1986) D. Reidel, Dordrecht, Holland). In the microfluidic sample cells of this invention, photocatalyst is preferably provided as a layer deposited on a surface within the sample channel and positioned to be irradiated by the UV source. The UV source is selected to provide illumination with energy equal to or higher than the semiconductor bandgap energy of the selected photocatalyst. Bandgap energies for a variety of semiconductor materials are well-known (S. R.

Morrison (1980) *Electrochemistry at Semiconductor and Oxidized Metal Electrodes*, Plenum Press, New York, N.Y.). Irradiation of the photocatalyst with light of energy equal to or higher than its bandgap results in the creation of holes, $h^+$, in the valence band and electrons (e−) in the conduction band of the semiconductor. These charge carriers diffuse to the surface of the photocatalyst to react with solution or surface absorbed species, e.g., water, to generate radicals, e.g., OH. or $O_2$—., which are known to oxidize organic carbon species. Metals of atomic number 44–47 and 76–79, particularly platinum, palladium, iridium, ruthenium, and rhodium added to or deposited on the surface of the semiconductor photocatalyst (providing a metalized photocatalysts) can enhance catalytic activity.

Preferred catalysts for TOC methods are based on $TiO_2$ with bandgap energy λ<about 380 nm. Illuminated $TiO_2$ semiconductor dispersions have, for example, been used to decompose selected organic wastes. Degussa P-25 has been identified as a commercial form of $TiO_2$ that is very active for photocatalysis of oxidation. This material consists primarily of the anatase form of $TiO_2$, being 80% (by weight) anatase with the remaining 20% the rutile form of $TiO_2$. Addition of certain metals to the $TiO_2$ surface is known to enhance photocatalytic activity (Izumi, I. et al. (1980) *J. Phys. Chem.* 80:3207). Addition of platinum metal, for example, to the $TiO_2$ surface is reported to dramatically enhance photocatalytic activity.

Properties of the thin-film $TiO_2$ that are believed to be associated with improved photocatalysis are a) anatase crystal structure, (b) small crystal size, (c) high porosity, and (d) large surface area. While the rutile structure is the most common form of $TiO_2$ obtained through crystal growth, the anatase form of $TiO_2$, however, generally exhibits higher catalytic activity and is thus preferred in this application. The presence of the anatase structure of $TiO_2$ in a given thin film material or foil can be assessed using X-ray diffraction methods. Crystal size, porosity and surface area of the catalyst can also influence catalytic activity, particularly in the present application, by affecting the contact area between the $TiO_2$ and organics in solution. These three properties are preferably selected to increase contact area. $TiO_2$ photocatalysts formed by electrochemical oxidation of Ti thin films and foils have properties associated with enhanced catalytic activity. Preferred $TiO_2$ photocatalysts for the present application can be formed by electrochemical oxidation of Ti thin films and foils as described for example in Turchi, C. S. and Ollis, D. F. (1990) *J. Catal.* 122:178; Kim, D. H. et al. (1995) *J. Env. Eng.* 121:590; Wahl, A. et al. (1995) *J. Electroanal. Chem.* 396:41; Kim, D. H. and Anderson, M. A. (1994) *Environ. Sci. Technol.* 28:479; Turchi, C. S. and Ollis, D. F. (1988) *J. Phys. Chem.* 92:6853; Al-Ekabi, H. and Serpone, N. (1988) *J. Phys. Chem.* 92:5726; Mathews, R. W. (1988) *J. Catal.* 111:264; Mathew, R. W. (1987) *J. Phys. Chem.* 91:3328. In particular, these literature methods have been applied to prepare photocatalysts by electrochemical oxidation of Ti thin films and foils in dilute $H_2SO_4$ solutions under galvanostatic control (Hitchinan, M. L. et al. (1996) *J. Chem. Soc. Faraday Trans.* 92:4049; Mikula, M. et al. (1992) *J. Electrochem. Soc.* 139:3470; Leitner, K. et al. (1986) *J. Electrochem. Soc.* 133:1561). As applied to preparation of $TiO_2$ photocatalysts for use in the TOC devices of this invention, thin-film $TiO_2$ prepared by electrochemical oxidation methods and having grain sizes on the order of a about a few hundred Angstrom have porosity sufficiently high and surface area sufficiently large to exhibit the desired improved photocatalytic properties. The thickness of the $TiO_2$ layer can be readily controlled by selection of the deposition conditions.

Mineralization of organics in the TOC devices of this invention can also be catalyzed using photoelectrocatalytic reactions. It is known that certain inorganic ions which may be present in semiconductor processing, such as sodium, potassium, calcium, ammonium, fluoride, chloride, nitrate, sulfate, and phosphate, suppress the activity of $TiO_2$ in photocatalytic reactions (Kim, D. H. and Anderson, M. A. (1994) *Environ. Sci. Technol.* 28:479). Application of a bias voltage ranging between about 0 to about 2 V (as measured vs. a saturated calomel electrode) to the $TiO_2$ catalyst with respect to a Ti counterelectrode can increase the catalytic activity or maintain high efficiency catalytic oxidation activity under adverse conditions such as the presence of interfering ions (up to about 1M concentrations) or in the absence of oxygen. Typically, catalyst performance can drop by about 25% in the presence of inorganic ions. Application of the bias voltage as described avoids this performance drop. In the device of this invention electrical contact with the $TiO_2$ catalyst is accomplished via the underlying Ti thin film which has been oxidized.

Photoelectrocatalysis is facilitated in devices of this invention (as illustrated, for example, in FIGS. 1F and 1G) by positioning a counterelectrode adjacent to the photocatalyst layer. A DC bias voltage is applied between the photocatalyst layer and its counterelectrode. The typical separation of the photocatalyst layer and its counterelectrode is 100 μm or less. The photocatalyst and its counterelectrode are both in contact with the water sample. The photocatalyst and its counterelectrode can be positioned at adjacent positions across the sample channel (FIG. 1G) or in close proximity to each other in the sample channel (e.g., on one side of the channel (top, bottom or wall thereof). The counterelectrode is preferably a think film or foil of a metal that is resistant to ultra pure water. A thin film or foil of titanium or zirconium is preferred.

In alternate specific embodiments, microfluidic TOC devices of this invention can employ $WO_3$-based photocatalysts. $WO_3$ semiconductors have a lower bandgap energy compared to $TiO_2$ materials allowing the use of lower energy light (λ≦about 480 nm) for illumination of the photocatalyst. The use of $WO_3$ photocatalysts facilitates lower cost TOC devices that may employ non-UV or near-UV sources, for example, LED (light emitting diode) and laser diode light sources. Photoelectrocatalysis can also be adapted for use with $WO_3$-based photocatalysts.

$TiO_2$ catalyst (and other semiconductor catalyst) layers may become poisoned, fouled, deactivated or degraded with time. Photocatalyst layers can be regenerated, for example as described in R. W. Matthews et al. (1990) *Analytica Chimica Acta* 222:171–179. Alternatively, microfluidic sample cells can be replaced when catalyst activity degrades.

Conductivity of a solution changes as a function of temperature. Accurate determination of concentration based on conductivity measurements requires temperature correction. Typically, conductivity measurements made at a temperature different from room temperature (i.e., 25° C.) are compensated to adjust the conductivity to what it would be at 25° C. Conductivity TOC devices of this invention provide for temperature measurement in the sample cell, preferably proximal to the conductivity electrodes. Temperature sensors of the illustrated devices are resistance temperature detectors. Illustrated temperature sensors 32 (e.g., FIGS. 1B–1D) can be thin-film resistors configured for two-probe measurement. Alternatively, thermistors or semiconductor temperature sensors can be employed.

Temperature compensation can also be achieved in the devices of this invention by controlling the temperature of the sample cell or sample channel. If such temperature control is employed it is preferred to minimize temperature change in the sample channel proximal to the conductivity electrodes to less than ±1° C.

Water samples to be analyzed using the TOC devices of this invention can be subjected to pretreatment steps, for example filtering steps and/or purification steps prior to TOC analysis to remove particulates or possible interferants of TOC detection.

The TOC measurement devices of this invention can be employed as components in a feedback control system or alarm system to detect an undesirable level of organics in a water supply or process line. For example, these TOC devices can be an element in a water purification system, particularly a system for production of ultra pure water, to assess the efficiency, or completeness of purification. Microfluidic TOC devices of this invention can be combined with purification systems, including for example, ion exchange or deionization, reverse osmosis, ultrafiltration, distillation and/or electrodialysis systems.

The devices of this invention are generally useful for the measurement of TOC in the range 0.001–100 ppm. The microfluidic TOC devices of this invention are particularly useful for the detection of low levels, up to about 5–10 ppm, of organic contaminants in ultrapure deionized water (e.g., in "18 Mega ohm" water). These microfluidic TOC devices are particularly useful in analysis of ultrapure water for applications to semiconductor fabrication which requires large amounts of ultra pure water for reaction and cleaning steps.

The following examples are provided to further illustrate the invention and are in no way intended to limit the scope of the invention.

EXAMPLES

Example 1

Immobilization of Platinized TiO$_2$ Photocatalyst

An optional photocatalyst element can be located in the microfluidic sample volume of the sample cells of this invention to enhance oxidation of organic species. The catalyst can be TiO$_2$ or a metalized TiO$_2$, such as platinized TiO$_2$. A TiO$_2$ catalyst element can be prepared as a layer on a surface within the sample volume. Aerosol-assisted MOCVD can be used, for example, to deposit a TiO$_2$ layer (Kodas, T. T. and M. J. Hampden-Smith (1994) *The Chemistry of Metal CVD* VCH Publishers, New York; and references therein). A 0.1 M solution of Titanium (IV)oxide acetylacetonate in methanol is sprayed onto a fused silica substrate held at a temperature sufficient to decompose the metal-organic precursor to TiO$_2$ (e.g., 400° C.) (Kodas and Hamden-Smith supra). An ultrasonic atomizer (Cole-Palmer) is used to create 10 to 30 µm size droplets for deposition. A shadow mask is used to pattern the TiO$_2$ on the substrate. The film prepared in this way is primarily a microcrystalline anatase phase, which has a higher photon efficiency than other phases and, hence, exhibits higher decomposition rates for organic species. The deposition conditions (substrate temperature, flow rate, deposition time, etc.) are selected to form thin TiO$_2$ films having high surface roughness. Rough films are formed when the gas transport kinetics are controlled by manipulating the concentration of the precursor depositing onto the hot substrate surface as described in Manginell, R. P. et al. (June 1996) *IEEE Solid-State Sensor and Actuator Workshop* (Hilton Head Island, S.C. p. 23). Rough thin films are preferred to enhance decomposition of organics by increasing the activity of the photocatalyst.

A metalized-TiO$_2$ layer is formed by precipitation of the metal from solution onto the TiO$_2$ layer. For example, platinized-TiO$_2$ is formed by precipitation of Pt from solution onto the TiO$_2$ layer. A methanol solution of chloroplatinic acid is spray deposited over the patterned TiO$_2$ layer on the substrate. Methanol is evaporated and the surface is exposed to 254 nm WV radiation to decompose chloroplatinic acid leaving dispersed Pt on the surface.

Example 2

Sample Conductivity Analysis Using a Microfluidic Sample Cell

Figure 3:
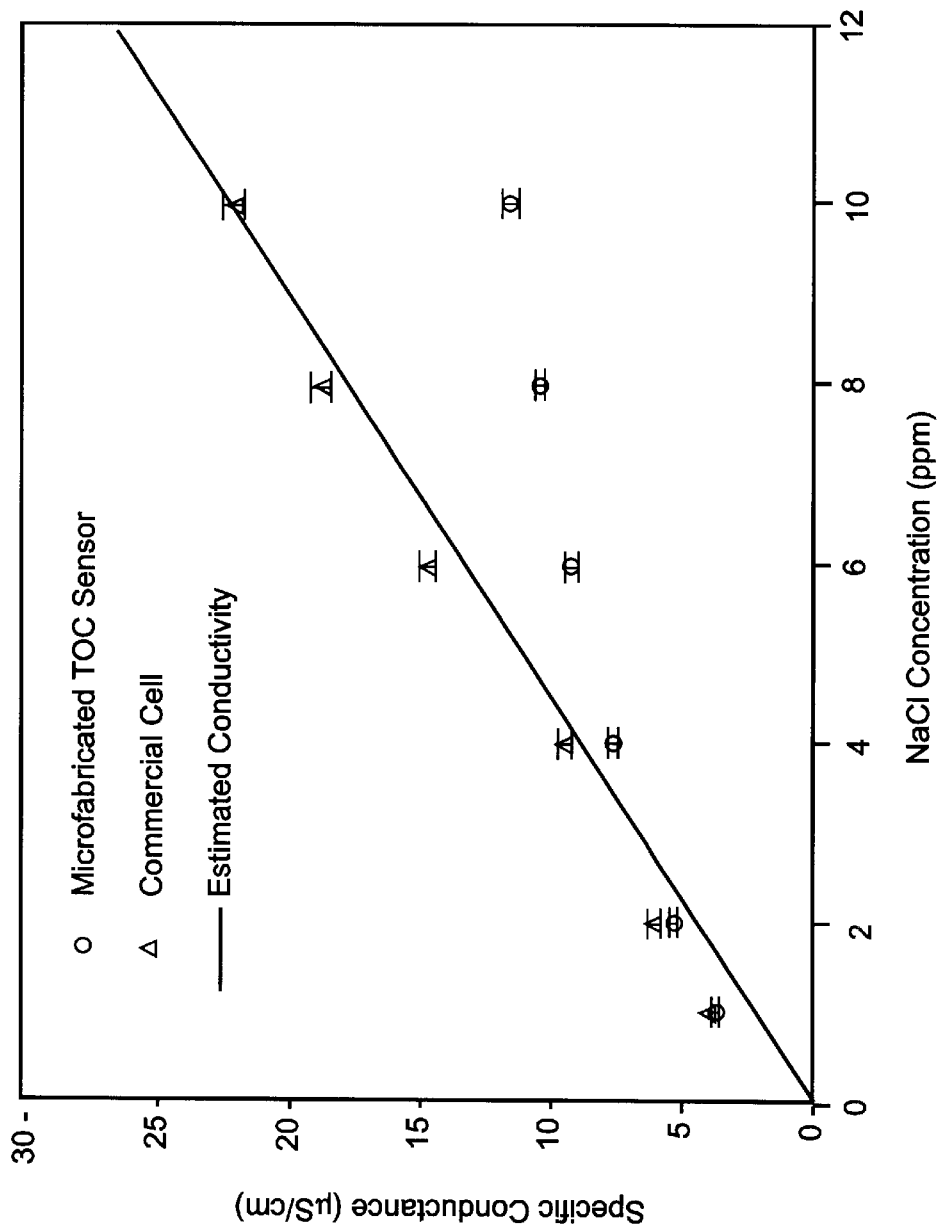
FIG. 3 is a graph of conductivity measurements of aqueous NaCl standard samples determined using a microfluidic TOC conductivity device of this invention (open circles) compared to measurements of the same samples with a commercial TOC device (open triangles) as described in Example 2.

A sample cell and device as in FIGS. 1 and 1A with sample volume thickness of 125 µm and having a platinized-TiO$_2$ photocatalytic layer within the sample volume, as described in Example 1, was employed to measure conductivity in aqueous NaCl standard samples of known concentration in the ppm range. FIG. 3 is a graph comparing conductivities of these standards measured with the microfluidic device system (open circles) to those (open triangle) measured using a commercial conductivity cell (VWR Conductivity Cell, Gold flow cell with a 10 cm$^{-1}$ cell constant). The solid line in the graph is the theoretical conductivity (C) calculated using the known molar ionic conductances of Na$^+$ ($\Lambda_0^+$=50.11 S/cm$^2$ mol) and Cl$^-$ ($\Lambda_0^-$=76.34 S/cm$^2$ mol) at infinite dilution and the concentration of the NaCl solution (mol/cm$^3$) in equations:

$$\Lambda_0 = \Lambda_0^+ + \Lambda_0^-$$

and $$C = \Lambda_c = \Lambda c$$

where $\Lambda$=molar conductance; $\Lambda_o$=limiting molar conductance at infinite dilution at 25° C.; and $\Lambda^-_o$ or $\Lambda^+_o$=limiting molar ionic conductances (anionic or cationic) at infinite dilution at 25° C. The data in FIG. 3 are the average of three separate measurements for each NaCl solution. The standard deviation for the measurement with either device is ±2%. The dynamic response of the microfluidic system was linear up to a conductivity of about 6 µS/cm. The response of the microfluidic system agreed with the commercial conductivity cell and with theoretical prediction at conductivity below about 6 µS/cm.

Figure 4:
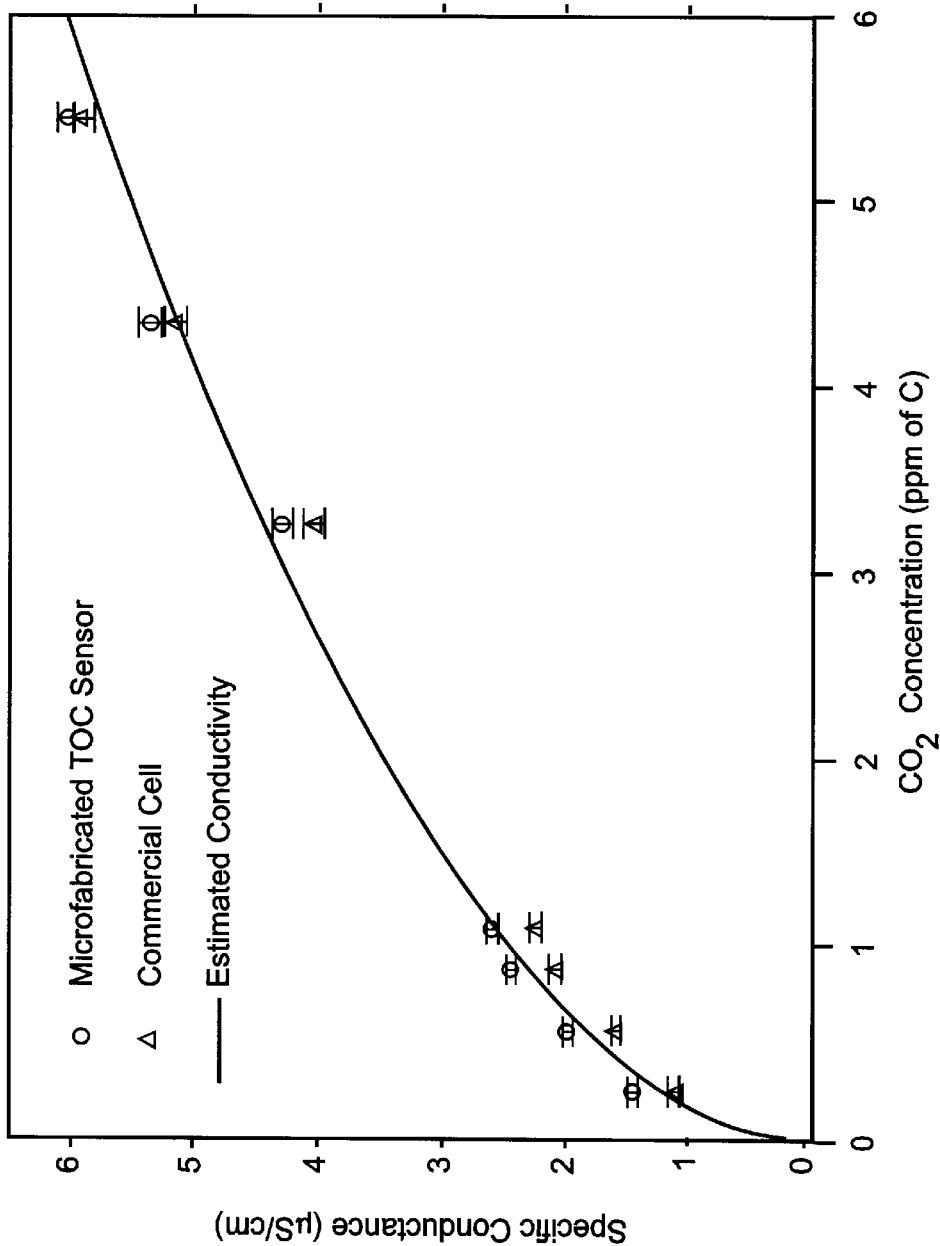
FIG. 4 is a graph of conductivity measurements of aqueous $CO_2$ samples determined using a microfluidic TOC conductivity device of this invention (open circles) compared to measurements of the same samples with a commercial TOC device (open triangles) as described in Example 2. The solid line represents a calculation of the conductivity of the samples.

The same microfluidic system was used to measure conductivity (open circles) of aqueous CO$_2$ solutions (conductivity) and its response is compared to that of a commercial TOC device (open triangles) as shown in FIG. 4. In this figure, CO$_2$ concentration is given in units of ppm. A commercial Shimadzu TOC analyzer (Model TOC-5000A) was used to calibrate CO$_2$ solution concentration. Data in FIG. 4 represent the average of three measurements with a standard deviation of ±3% for the microfluidic system and ±2% for the commercial conductivity cell. The solid line in the graph is a calculation of conductivity using the dissociation constant of carbonic acid, the ion-product constant of water and the equivalent conductances of the ions present.

For concentrations of carbon higher than 3 ppb, the correlation between the change in CO$_2$ concentration and conductivity is expressed by:

$$\log\left(\frac{c_1}{c_2}\right) = n\log\left(\frac{C_1}{C_2}\right)$$

where c is $CO_2$ concentration, C is conductivity, subscripts indicate different concentrations and n is a constant. This relationship was used to verify the response of the TOC analysis system and provided a basis to calibrate measured TOC levels using a simple analytical expression. Results obtained with the microfluidic TOC measurement system agreed well with the commercial conductivity cell and previous literature (Poirier, S. J. and J. H. Wood (1978) American Laboratory, December: 79–89).

Example 3

Measurement of Methanol in Aqueous Solutions

Figure 5:
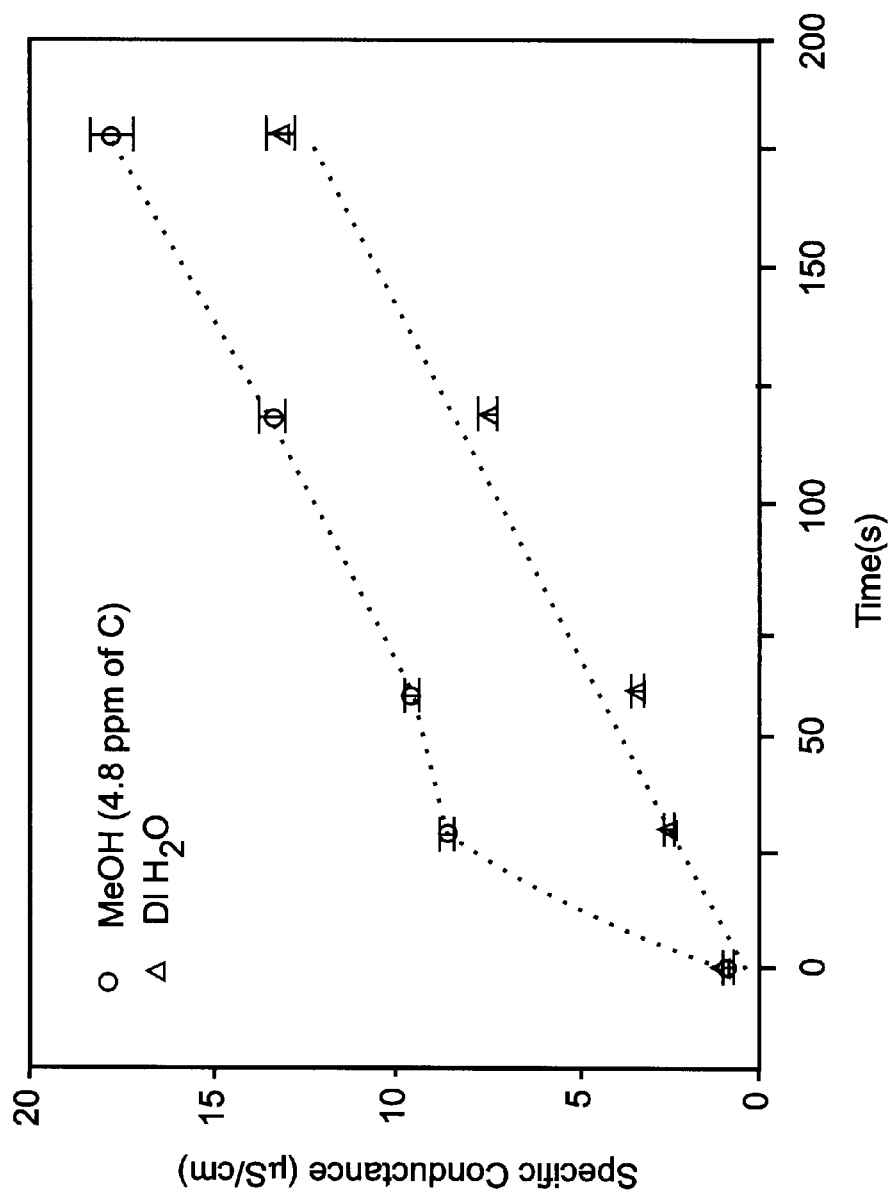
FIG. 5 is a graph of conductivity as a function of irradiation time of a 4.8 ppm methanol solution measured in a microfluidic TOC conductivity device (open circles), as described in Example 3. These data are compared in the graph to conductivity of a deionized water sample as a function of irradiation time in the same device.

A sample cell and device as in FIGS. 1 and 1A with sample volume thickness of 125 $\mu$m and having a platinized-$TiO_2$ photocatalytic layer as described in Example 1 was employed to measure conductivity of aqueous methanol solutions. The concentrations of methanol were standardized using a TOC analyzer by subtracting the inorganic carbon fraction from the total carbon to arrive at TOC. FIG. 5 is a graph of conductivity as a function of irradiation time of a 4.8 ppm methanol solution (open circles) compared to conductivity of deionized water under the same irradiation conditions (open triangles). Measurements were performed by introducing a sample into the microfluidic sample cell, stopping the liquid flow, exposing the sample volume to UV radiation and monitoring the response of the conductivity meter and ohm meter. Temperature in the proximity of the electrode was measured and conductivity measurements were corrected, if necessary, for changes in temperature.

For methanol samples a large increase in conductivity was observed in the first 30 sec. of irradiation of the sample. This represented the complete mineralization of methanol in the sample. At times longer than about 60 sec., the conductivity increased at a constant rate, representing instrumental drift in conductance. Identical measurements performed on deionized water samples (open triangles) also showed a constant increase of conductance with time with a rate nearly identical to that observed at longer times with methanol solutions. The conductivity of the 4.8 ppm aqueous methanol solution at 30 sec. was measured to be 8.2 $\mu$S/cm. At the same time, the conductivity of the deionized water control was 2.6 $\mu$S/cm. Correcting for the conductivity of the control, a value of 5.6 $\mu$S/cm was obtained. The conductivity of a 4.8 ppm sample of aqueous methanol should be 5.4 $\mu$S/cm. See: Keene, F. R. (1993) *Electrochemical and Electrocatalytic Reactions of Carbon Dioxide* (B. Sullivan et al. eds.) Elsevier, N.Y. The close agreement of the value measured for the conductivity of the methanol solution and that of the Keene reference validates the performance of the TOC analysis system of this invention.

Figure 6:
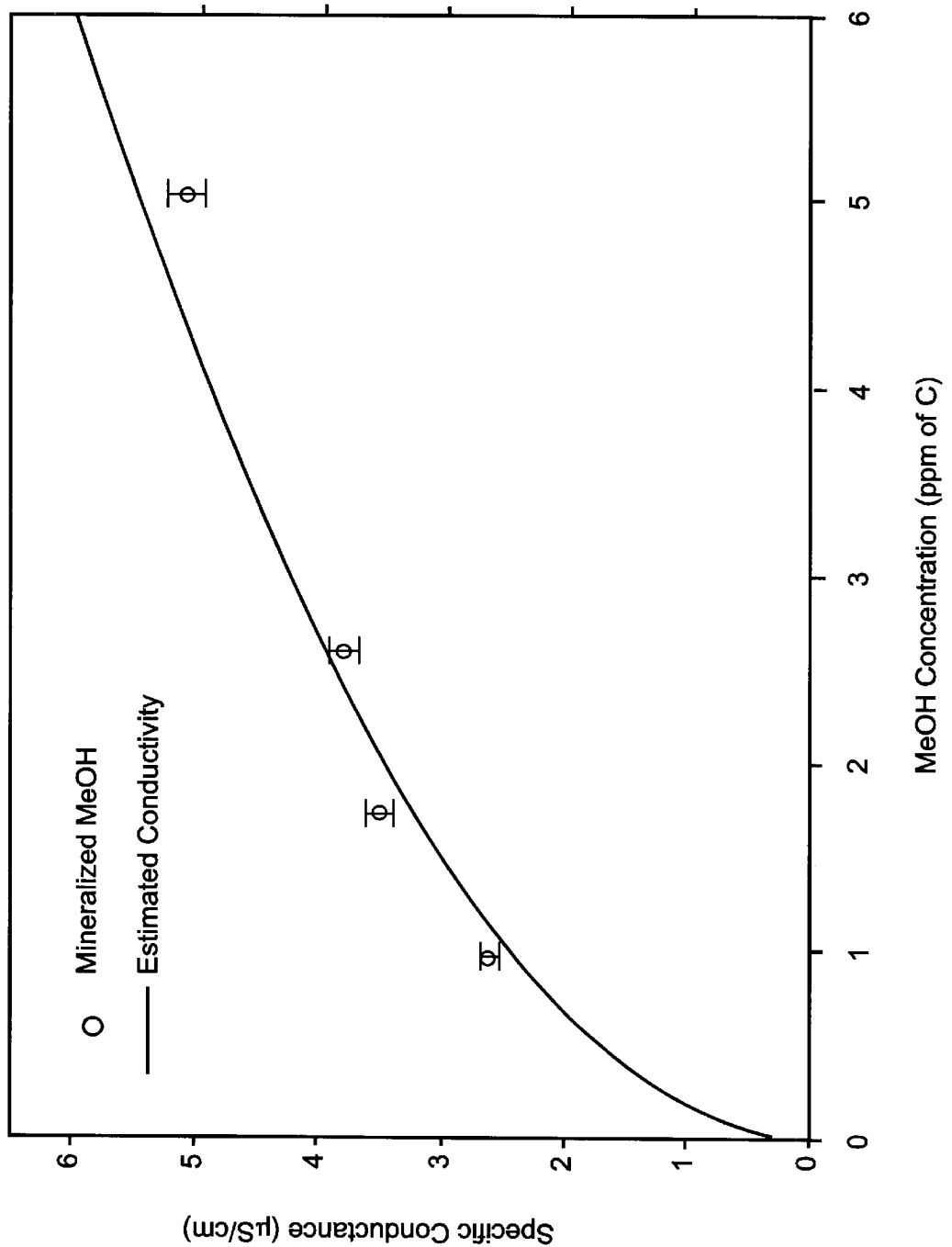
FIG. 6 is a graph of conductivity of a series of aqueous methanol solutions of known concentration measured after irradiation in a TOC device of this invention. The conductivity measurements are corrected for background conductivity in deionized water samples as described in Example 3.

FIG. 6 is a plot of corrected conductivity for a series of aqueous methanol solutions of known concentration. Each data point (open circles) represents the average of three measurements and the standard deviation is ±3%. The solid line represents the theoretical calculation of conductivity for the standard solutions.

Those of ordinary skill in the art will appreciate that materials, techniques and procedures, other than those specifically exemplifies herein, can be employed in the practice of this invention. A variety of alternative materials that function in an equivalent way to those herein exemplified may be known in the art and can be readily employed or readily adapted for use in this invention. For example, alternative materials for cell substrates and membranes and alternative techniques for sealing, etching, micromachining and construction of sample cells are known and available in the art. Likewise, alternative photocatalysts are known and available in the art. All such art-recognized alternatives and functional equivalents can be employed in the practice of this invention and are encompassed by this invention.

We claim:

1. A device for measurement of total organic carbon in a water sample which comprises a UV source, a microfluidic sample cell which is at least in part transparent to UV radiation and which has at least one sample channel for receiving the water sample, the sample cell comprising a photocatalyst in contact with the water sample and the sample cell being positioned with respect to the UV source such that at least a portion of a water sample in the sample channel can be irradiated by the UV source to oxidize organics in the water sample and generate $CO_2$, a means for detecting the $CO_2$ generated to determine the total organic carbon in the sample, and a counterelectrode in proximity to the photocatalyst layer so that a bias voltage can be applied to the photocatalyst layer wherein the photocatalyst is a thin-film or layer in the sample channel.

2. The device of claim 1 wherein the photocatalyst is a thin-film of $TiO_2$ and the counter electrode is a thin-film of Titanium metal.

3. A device for measurement of total organic carbon in a water sample which comprises a UV source, a microfluidic sample cell which is at least in part transparent to UV radiation and which has at least one sample channel for receiving the water sample, the sample cell positioned with respect to the UV source such that at least a portion of a water sample in the sample channel can be irradiated by the UV source to oxidize organics in the water sample and generate $CO_2$, a means for detecting the $CO_2$ generated to determine the total organic carbon in the sample and a device holder for receiving the microfluidic cell and UV source and holding these elements in a fixed relative position such that at least a portion of the sample in the sample channel is irradated by the UV source, wherein the microfluidic sample cell comprises a top substrate and a bottom substrate and an intervening shaped spacer having a cavity therein which together form the sample channel the cavity defining the shape and size of the sample channel, a sample inlet and a sample outlet in the sample cell, a photocatalyst element in contact with the sample and a first and second conductivity electrode positioned within the sample channel wherein the photocatalyst is positioned in the sample channel to be irradiated by the UV light source.

4. The device of claim 3 wherein the UV source is positioned adjacent to the top substrate of the cell, the photocatalyst layer is formed on the bottom substrate and the first and second conductivity electrodes are formed on the top and the bottom substrates, respectively.

5. A device for measurement of total organic carbon in a water sample which comprises a UV source, a microfluidic sample cell which is at least in part transparent to UV radiation and which has at least one sample channel for receiving the water sample, the sample cell positioned with respect to the UV source such that at least a portion of a water sample in the sample channel can be irradiated by the UV source to oxidize organics in the water sample and generate $CO_2$, a means for detecting the $CO_2$ generated to determine the total organic carbon in the sample, and a photocatalyst layer in the sample flow path, wherein the sample cell is a continuous flow cell and comprises a sample flow path and a control flow path, wherein the sample passing through the control flow path is not irradiated by the UV source, wherein a portion of the top substrate is not transparent to UV radiation and wherein a photocatalyst element is provided on the bottom substrate, the photocatalyst element positioned with respect to the top substrate such that it is irradiated with UV radiation.

6. A device for measurement of total organic carbon in a water sample which comprises a UV source, a microfluidic sample cell which is a continuous flow cell, which is at least in part transparent to UV radiation and which has at least one sample channel for receiving the water sample, the sample cell positioned with respect to the UV source such that at least a portion of a water sample in the sample channel can be irradiated by the UV source to oxidize organics in the water sample and generate $CO_2$, a nondispersive infrared spectroscopy (NDIR) detector for measurement of $CO_2$ generated by UV irradiation in the flow path of the flow sample cell and determination of the total organic carbon in the sample, and a conduit for conducting samples from the sample cell into the NDIR detector.

7. The device of claim 6 wherein the conduit is heated to avoid condensation of the sample.

8. A device for measurement of total organic carbon in a water sample which comprises a UV source, a microfluidic sample cell which is a continuous flow cell, which is at least in part transparent to UV radiation and which has at least one sample channel for receiving the water sample, the sample cell positioned with respect to the UV source such that at least a portion of a water sample in the sample channel can be irradiated by the UV source to oxidize organics in the water sample and generate $CO_2$, an NDIR detector for measurement of $CO_2$ generated by UV irradiation in the flow path of the flow sample cell and determination of the total organic carbon in the sample, wherein the NDIR detector comprises a long pathlength gas cell, an infrared source for irradiating the gas cell and an infrared detector to measure $CO_2$ in the gas cell.

9. A device for measurement of total organic carbon in a water sample which comprises a UV source, a microfluidic sample cell which is at least in part transparent to UV radiation and which has at least one sample channel for receiving the water sample, the sample cell positioned with respect to the UV source such that at least a portion of a water sample in the sample channel can be irradiated by the UV source to oxidize organics in the water sample and generate $CO_2$ and a means for detecting the $CO_2$ generated to determine the total organic carbon in the sample, wherein the water sample being irradiated is confined to a layer perpendicular to the direction of the irradiating light, wherein the thickness of the layer is less than about 150 $\mu$m and wherein the UV radiation provides substantially complete oxidation of organic carbon in the irradiated sample within about 30 seconds.

10. A method for detecting total organic carbon in a water sample which comprises introducing the water sample into a microfluidic sample cell and mineralizing the organic carbon therein to $CO_2$ by irradiating the water sample with UV radiation and measuring the amount of $CO_2$ generated in the sample channel on irradiation, wherein the water sample being irradiated is confined to a layer perpendicular to the direction of the irradiating light, wherein the thickness of the layer is less than about 150 $\mu$m and wherein tile UV radiation provides substantially complete oxidation of organic carbon in the irradiated sample within about 30 seconds.

11. The device of claim 9 wherein the microfluidic sample cell comprises two overlayered substrates at least one of which has a cavity on its internal surface which forms a sample channel.

12. The device of claim 9 wherein the microfluidic sample cell comprises two overlayered substrates and an intervening spacer which forms a sample channel.

13. The device of claim 9 wherein the sample cell comprises electrodes in contact with the irradiated sample to measure conductivity of that sample and to thereby detect and measure $CO_2$ generated in that sample.

14. The device of claim 9 wherein the sample cell comprises a photocatalyst in contact with the water sample.

15. The device of claim 14 wherein the photocatalyst comprises a semiconductor material.

16. The device of claim 15 wherein the photocatalyst is $TiO_2$.

17. The device of claim 16 wherein the photocatalyst is metalized $TiO_2$.

18. The device of claim 16 wherein the photocatalyst is platinized $TiO_2$.

19. The device of claim 16 wherein the photocatalyst is $TiO_2$ formed by electrochemical oxidation of a Ti thin film or foil.

20. The device of claim 9 wherein the microfluidic sample cell comprises a top substrate and a bottom substrate and an intervening shaped spacer having a cavity therein which together form the sample channel the cavity defining the shape and size of the sample channel, a sample inlet and a sample outlet in the sample cell, a photocatalyst element in contact with the sample and a first and second conductivity electrode positioned within the sample channel wherein the photocatalyst is positioned in the sample channel to be irradiated by the UV light source.

21. The device of claim 20 wherein the sample cell further comprises a temperature sensor in contact with the sample in the sample channel.

22. The device of claim 21 wherein the conductivity electrodes are microfabricated using photolithography on one or both of the substrates.

23. The device of claim 9 wherein the sample cell is a static flow cell or a stop flow cell.

24. The device of claim 9 wherein the sample cell is a continuous flow cell.

25. The device of claim 24 wherein the sample cell comprises a sample flow path and a control flow path.

26. The device of claim 25 wherein the sample passing through the control flow path is not irradiated by the UV source.

27. The device of claim 25 wherein the sample cell comprises a top substrate, a bottom substrate and an intervening spacer having at least one shaped cavity therein which together form the sample cell and wherein the cavity in the spacer forms the flow paths in the cell.

28. The device of claim 26 further comprising a UV radiation filter to block UV irradiation of the sample in the control channel.

29. The device of claim 26 further comprising a photocatalyst layer in the sample flow path.

30. The device of claim 24 further comprising an NDIR detector for measurement of $CO_2$ generated by UV irradiation in the flow path of the flow sample cell.

31. The method of claim 10 wherein $CO_2$ generated by irradiation is detected by conductivity measurements.

32. The method of claim 10 wherein $CO_2$ generated by irradiation is detected by NDIR.

* * * * *

UNITED STATES PATENT AND TRADEMARK OFFICE
CERTIFICATE OF CORRECTION

PATENT NO. : 6,444,474 B1 Page 1 of 1
DATED : September 3, 2002
INVENTOR(S) : Thomas et al.

It is certified that error appears in the above-identified patent and that said Letters Patent is hereby corrected as shown below:

Title page,
Reference "Mathews, R.W.", please replace "Mathews" with -- Matthews --.
Reference "Mathews, R.W.", please replace "Mathews" with -- Matthews --.

Column 8,
Line 41, please insert -- 5 -- after "fluid inlet".

Column 14,
Line 28, please replace "being" with -- are --.

Column 15,
Line 9, please replace "OH." with -- OH • --.
Line 52, please replace "Mathew" with -- Matthews --.
Line 63, please replace "Angstrom" with -- Angstroms --.

Column 16,
Line 33, please replace "think" with -- thin --.

Column 18,
Line 38, please replace "C=Λc=Λc " with -- C=Λc=$Λ_0$c --.

Column 19,
Line 65, please replace "exemplifies" with -- exemplified --.

Column 21,
Line 55, please replace "tile" with -- the --.

Signed and Sealed this

Fourth Day of March, 2003

JAMES E. ROGAN
*Director of the United States Patent and Trademark Office*